US011775932B2

(12) United States Patent
Chan et al.

(10) Patent No.: US 11,775,932 B2
(45) Date of Patent: *Oct. 3, 2023

(54) HIGH FIDELITY CLINICAL DOCUMENTATION IMPROVEMENT (CDI) SMART SCORING SYSTEMS AND METHODS

(71) Applicant: Iodine Software, LLC., Austin, TX (US)

(72) Inventors: William Chan, Austin, TX (US); W. Lance Eason, Austin, TX (US); Timothy Harper, Austin, TX (US); Bryan Horne, Austin, TX (US); Michael Kadyan, Austin, TX (US); Jonathan Matthews, Dripping Springs, TX (US); Joshua Toub, Menlo Park, CA (US)

(73) Assignee: Iodine Software, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,801

(22) Filed: Jul. 11, 2022

(65) Prior Publication Data
US 2022/0343280 A1   Oct. 27, 2022

Related U.S. Application Data

(63) Continuation of application No. 16/939,790, filed on Jul. 27, 2020, now Pat. No. 11,423,356, which is a
(Continued)

(51) Int. Cl.
*G06Q 10/10* (2023.01)
*G06Q 50/22* (2018.01)
(Continued)

(52) U.S. Cl.
CPC ............... *G06Q 10/10* (2013.01); *G06N 7/01* (2023.01); *G06N 20/00* (2019.01); *G06Q 50/22* (2013.01); *G16H 50/20* (2018.01); *G16H 50/30* (2018.01)

(58) Field of Classification Search
CPC .......... G06Q 10/10; G06Q 50/22; G06N 7/01; G06N 20/00; G06N 20/20; G06N 3/045;
(Continued)

(56) References Cited

U.S. PATENT DOCUMENTS

| 10,394,871 B2 * | 8/2019 | Galia ..................... G06Q 40/08 |
| 2011/0082712 A1 * | 4/2011 | Eberhardt, III ........ G16H 50/30 705/4 |

(Continued)

OTHER PUBLICATIONS

Kuhn et al., Clinical Documentation In The 21st Century: Executive Summary Of A Policy Position Paper From The American College Of Physicians, Annals Of Internal Medicine, vol. 162, No. 4, Feb. 17, 2015, 14 pages (Year: 2015).*
(Continued)

*Primary Examiner* — Joy Chng
(74) *Attorney, Agent, or Firm* — Sprinkle IP Law Group

(57) ABSTRACT

A clinical documentation improvement (CDI) smart scoring method may include predicting, via per-condition diagnosis machine learning (ML) models and based on clinical evidence received by a system, a probability that a medical condition is under-documented and, via per-condition documentation ML models and based on documentation received by the system, a probability that a medical condition is over-documented. The under- and over-documentation scores are combined in view of special indicators and queryability factors, which can also be evaluated using ML query prediction models, to generate an initial CDI score. This CDI score can be further adjusted, if necessary or desired, to account for factors such as length of stay, payer,
(Continued)

patient location, CDI review timing, etc. The final CDI score can be used to prioritize patient cases for review by CDI specialists to quickly and efficiently identify meaningful CDI opportunities.

20 Claims, 11 Drawing Sheets

Related U.S. Application Data continuation of application No. 15/349,679, filed on Nov. 11, 2016, now Pat. No. 10,733,566.

(51) Int. Cl.
*G16H 50/30* (2018.01)
*G16H 50/20* (2018.01)
*G06N 20/00* (2019.01)
*G06N 7/01* (2023.01)

(58) Field of Classification Search
CPC ........... G06N 3/08; G06N 5/01; G16H 50/30; G16H 15/00; G16H 40/20; G16H 40/67
USPC ........................................................ 705/2–3
See application file for complete search history.

(56) References Cited

U.S. PATENT DOCUMENTS

| | | | | |
|---|---|---|---|---|
| 2012/0215551 A1* | 8/2012 | Flanagan | ............... | G16H 50/20 705/2 |
| 2012/0304054 A1* | 11/2012 | Orf | ........................ | G16H 40/20 715/255 |
| 2013/0080187 A1* | 3/2013 | Bacon | .................... | G16H 70/60 705/3 |
| 2013/0297348 A1* | 11/2013 | Cardoza | ................. | G16H 40/20 705/3 |
| 2016/0012187 A1* | 1/2016 | Zasowski | ............... | G06Q 10/10 705/3 |

OTHER PUBLICATIONS

Optum, Insights And Best Practices For Clinical Documentation Improvement Programs, Jan. 15, 2015, https://www.optum.com/content/dam/optum3/optum/en/resources/white-papers/EHR.BestPracticesforClinicalDocumentationImprovement.pdf, 6 pages (Year: 2015).*

* cited by examiner

| | 432 | 402 | 404 | 406 | 408 | 410 | 412 | 414 |
|---|---|---|---|---|---|---|---|---|
| | Inpatient (4/9) | Mortality | Queried | Discharged | ▽ Filters (County ...) | +◨ Search by Patient ⊗ 🖨 ⟳ | | |
| | Patients | | Location | Payer | Conditions 424 | Q | LOS\|GMLOS | Reviewed |
| ▽ Priority Cases: 4 cases | | 418 | 420 | 422 | | | 428 | 430 |
| | Frost, Kimberly —416 ⊙⊙⊙○ ▾ | | 25-4N | WC | [S] Hyponatremia | | 9d\|- | Never |
| | Lewis, Rex ⊙⊙⊙○ ▾ | | 84-4N | MCARE | [S] Obesity [Myocardial isch...] | Ⓠ | 4d\|- | Never |
| | Macias, Elianna ⊙⊙⊙○ ▾ | | 10-4N | MCARE | [S] Chronic renal f... [Anemia] [+1] | | 3d\|3.0d | 9/11 |
| | Hutchinson, Aldo ⊙⊙⊙○ ▾ | | 27-4N | TEST | [S] Heart failure [Anemia] | | 30d\|- | 🗓 Never |
| ▷ Low Priority Cases: 5 cases —434 | | | | | | | | |
| ▷ Out of Scope Payers: 0 cases | | | | | | | | |
| ▷ Reviewed Today: 0 cases | | | | | | | | |

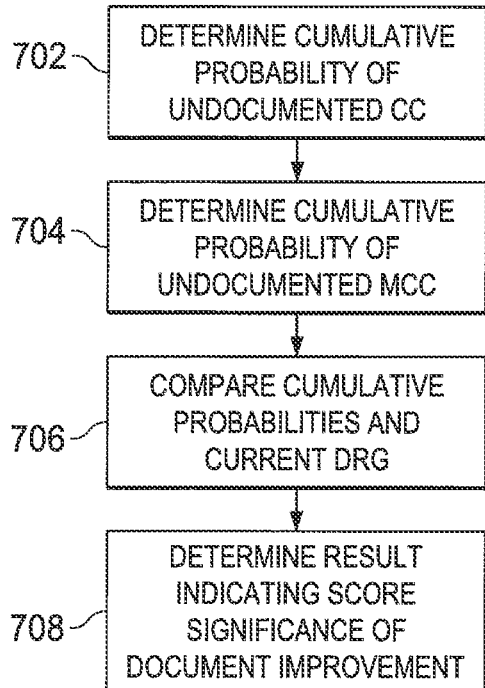
FIG. 7
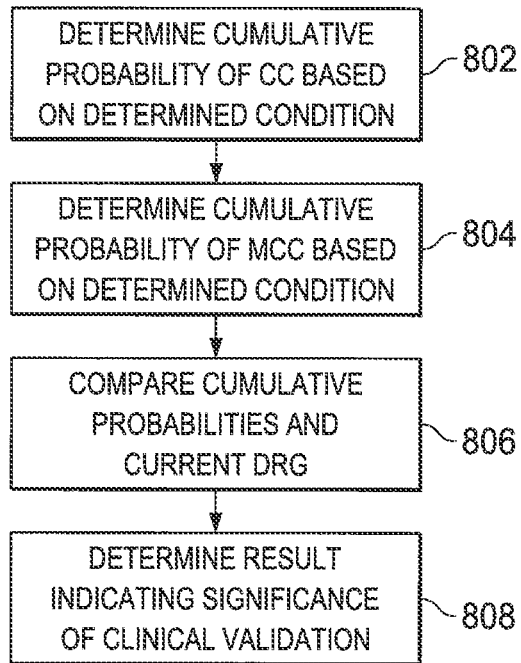
FIG. 8
| CONDITION | ASSIGNED PROBABILITY VALUE |
|---|---|
| SURGERY | .23 |
| ICU | .46 |
| PALLIATIVE CARE | .15 |
| ○<br>○<br>○ | ○<br>○<br>○ |
FIG. 9

HIGH FIDELITY CLINICAL DOCUMENTATION IMPROVEMENT (CDI) SMART SCORING SYSTEMS AND METHODS

CROSS-REFERENCE TO RELATED APPLICATION(S)

This application is a continuation of, and claims a benefit of priority under 35 U.S.C. § 120 from U.S. patent application Ser. No. 16/939,790, filed Jul. 27, 2020, issued as U.S. Pat. No. 11,423,356, entitled "HIGH FIDELITY CLINICAL DOCUMENTATION IMPROVEMENT (CDI) SMART SCORING SYSTEMS AND METHODS," which is a continuation of, and claims a benefit of priority under 35 U.S.C. § 120 from U.S. patent application Ser. No. 15/349,679, filed Nov. 11, 2016, issued as U.S. Pat. No. 10,733,566, entitled "HIGH FIDELITY CLINICAL DOCUMENTATION IMPROVEMENT (CDI) SMART SCORING SYSTEMS AND METHODS," both of which are fully incorporated by reference herein for all purposes.

TECHNICAL FIELD

This disclosure relates generally to networked systems configured for electronically monitoring patient records and identifying those cases that are most likely to have documentation query opportunities. More particularly, embodiments disclosed herein relate to a system, method, and computer program product for receiving large quantities of real-time hospital data and clinical documentation, reviewing and analyzing received real-time data, extrapolating a high fidelity numerical value representing a significance or level of potential clinical documentation improvement over given clinical documentation about a patient's case, useful for prioritizing patient charts for review.

BACKGROUND OF THE RELATED ART

Clinical documentation improvement (CDI) refers to a process used in healthcare facilities such as hospitals. A health information management (HIM) or CDI specialist's job is to review the information that a physician has documented about a patient in order to ensure that the documentation is accurate and complete. This process can be labor intensive because it requires the CDI specialist to understand the clinical needs of the patient and is able to find the gaps in the documentation in the patient's chart.

Currently, most CDI specialists do not have the capacity to review every patient chart and also re-review those charts on a regular (24-hour) basis to check for any physician updates that would affect the prioritization of review. Thus, a CDI specialist typically reviews patient charts in a somewhat random fashion, or they may employ relatively limited techniques for prioritizing how they review patient charts. Some examples of these methods are as follows:

(a) CDI specialists first review patient charts that have been in the hospital the longest and then work their way to the patients who were recently admitted to the hospital last. This method is inadequate because patients who only stay in the hospital for 1-2 days will likely never have their charts reviewed for clinical documentation improvement.

(b) A CDI specialist will perform reviews on brand new patients (i.e., patients whose charts have not yet been reviewed by a CDI specialist) in the mornings, and perform re-reviews (i.e., reviews on charts that have already been reviewed at least once) in the afternoons. This method is inadequate because it is focused on dedicating an equal amount of effort to initial reviews and re-reviews even though charts that need an initial review may have significantly more opportunity for clinical documentation improvement on a given day and vice-versa.

(c) Some CDI specialists use technology tools to scan documentation and flag the patient charts that should be reviewed. This method is inadequate because it flags the patient charts without differentiating which one(s) would be more important than others. Thus, every patient chart that is flagged is equally important to another patient chart that is flagged for review. Therefore, if a CDI specialist only has time to review, for example, 10 of the 12 charts that are flagged, two charts may be neglected completely at random, regardless of whether they might yield the most significant clinical documentation improvement.

Conventional CDI systems and programs have no way of separating cases that present document query opportunities improvement opportunities from cases that do not. Furthermore, conventional CDI systems and programs may not distinguish documentation improvement opportunities (e.g., ensuring each patient's condition is properly documented) from clinical validation opportunities (e.g., ensuring conditions reported in a patient's documentation are actually present in the patient's case). Heuristics—such as reviewing all Medicare patients first, ordering by length of stay, etc.—may be used to provide some order to the review process, but these approaches have limitations.

Moreover, conventional CDI systems and programs do not provide adequate mechanisms for identifying which cases should be re-reviewed. Because each patient's condition, treatment, and documentation may change during the course of each day of a patient's stay (also referred to herein as a "visit"), it is possible that a patient without documentation improvement opportunity on day 2 may have an opportunity on day 3—or vice versa. A patient's condition might worsen, new results might indicate a worse condition than the data available originally seemed to indicate, or conversely, a physician might update the documentation without CDI intervention, thereby negating a prior documentation issue. Here, conventional CDI systems and programs would also come up short, as they are unable to monitor how documentation needs change over time.

Further, conventional CDI systems and programs may only focus on one side of the clinical documentation equation, for instance, by considering only opportunities for document improvement in cases where a patient's actual condition might be more severe than what is reflected in the documentation. Such systems may not adequately identify instances of over-documentation, where the patient's file indicates conditions beyond those from which the patient is actually suffering.

SUMMARY OF THE DISCLOSURE

Clinical documentation is at the core of every patient encounter. It must be accurate, timely, and reflect the scope of services provided. CDI can facilitate the accurate representation of a patient's clinical status that translates into coded data, which can then be translated into hospital quality report cards, physician report cards, reimbursement, public health data, and so on. As the demand for accurate and timely clinical documentation continues to increase, there is room for innovations and improvements.

Accordingly, an object of the disclosure is to provide new CDI systems, methods, and computer program products that can monitor real-time patient data, identify cases that are most likely to have documentation query opportunities, factually and accurately assess both under- and over-documentation of patient data, and generate, in real-time, a prioritized list of cases which present opportunities to improve clinical documentation.

This object can be realized in high fidelity (i.e., high factual accuracy in reporting facts or details) CDI systems, methods, and computer program products particularly configured for reviewing and analyzing real-time clinical documentation and hospital data for real-time maintenance and updating a list of patient cases prioritized by CDI scores (and/or levels) such that a CDI specialist can efficiently and effectively initiate a query to resolve an identified documentation problem.

Deployed in an average hospital, embodiments can expect to receive one million or more pieces of data per day. Embodiments continuously process this data to score each patient for query opportunities. For each patient case, embodiments determine a probabilistic CDI score, and embodiments generate an interface providing a list of patient cases ranked by the determined CDI score. CDI specialists have a limited time to review a finite number of patient cases (also referred to as charts). This approach allows them to focus on the charts that have the most opportunity for clinical documentation improvement and, as a result, ensures that the documentation is accurate and corresponds to care delivered as well as the diagnoses that are being made about the patient. Another benefit of this approach is that accurate documentation can lead to accurate billing and reimbursement rates for the hospital that employs embodiments of the real-time medical communication system described herein.

According to some embodiments, real-time generation and maintenance of a prioritized list of cases for which CDI opportunities exist may take the following steps: (1) predicting, based on clinical evidence in hospital data and documentation received by the real-time medical communication system, which medical conditions each patient has; (2) predicting, based on electronic documentation received by the real-time medical communication system, which medical conditions have been documented; (3) identifying which conditions have likely been under- or over-documented and calculate, for each condition associated with each patient, the probability that a CDI opportunity exists for each condition; (4) identifying other factors which might impact case queryability, such as the number of times the case has been reviewed, how many times the case may have already been queried, and how much documentation improvement opportunity likely remains on the case; (5) running the individual condition probabilities and the other factors through a Machine Learning (ML) algorithm to derive the probability that the case as a whole has a document improvement and/or clinical validation opportunity; (6) considering special indicators, such as palliative care, which can affect the existence of a document improvement and/or clinical validation opportunity; (7) returning a quantification of the CDI for the case; and (8) generating an interface providing an updated and prioritized list of cases for which query opportunities may exist.

In some embodiments, methods for real-time generation and maintenance of a prioritized list of cases for which CDI opportunities exist may comprise: receiving clinical data and documentation, parsing clinical data and documentation, determining patient conditions from entities parsed from clinical data and documentation, retrieving a patient's visit history, determining models for the one or more determined patient conditions, running the determined models, re-evaluating patient cases with the model outputs, generating a CDI score, and generating an interface based on the returned CDI scores.

In some embodiments, one or more adjustments to an initially determined CDI score may be applied for various purposes. These may include a length of stay adjustment, a documentation accuracy adjustment, a payer adjustment, a patient location adjustment, a documentation novelty adjustment, a review timing adjustment, a case size adjustment, and/or a documentation sufficiency adjustment.

One embodiment comprises a system comprising at least one processor and at least one non-transitory computer-readable storage medium that stores computer instructions translatable by the at least one processor to perform a method substantially as described herein. Another embodiment comprises a computer program product having a non-transitory computer-readable storage medium that stores computer instructions translatable by a processor to perform a method substantially as described herein. Numerous other embodiments are also possible.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made within the scope of the disclosure without departing from the spirit thereof, and the disclosure includes all such substitutions, modifications, additions and/or rearrangements.

BRIEF DESCRIPTION OF THE DRAWINGS

The drawings accompanying and forming part of this specification are included to depict certain aspects of the disclosure. It should be noted that the features illustrated in the drawings are not necessarily drawn to scale. A more complete understanding of the disclosure and the advantages thereof may be acquired by referring to the following description, taken in conjunction with the accompanying drawings in which like reference numbers indicate like features and wherein:

FIG. 4 depicts a diagrammatic representation of one example of a graphical user interface showing a list of patient cases prioritized by CDI scores (and/or levels) according to some embodiments disclosed herein.

FIG. 5A depicts a diagrammatic representation of another example of a graphical user interface showing a determined medical condition for a patient according to some embodiments disclosed herein.

FIG. 7 is a flowchart illustrating one example of determining the significance of a potential document improvement opportunity according to some embodiments disclosed herein.

FIG. 8 is a flowchart illustrating one example of a process for determining the significance of a potential clinical validation opportunity according to some embodiments disclosed herein.

FIG. 9 depicts a diagrammatic representation of an example of a set of special indicators for a query scoring method according to some embodiments disclosed herein.

DETAILED DESCRIPTION

The disclosure and various features and advantageous details thereof are explained more fully with reference to the exemplary and, therefore, non-limiting embodiments illustrated in the accompanying drawings and detailed in the following description. It should be understood, however, that the detailed description and the specific examples, while indicating the preferred embodiments, are given by way of illustration only and not by way of limitation. Descriptions of known programming techniques, computer software, hardware, operating platforms and protocols may be omitted so as not to unnecessarily obscure the disclosure in detail. Various substitutions, modifications, additions and/or rearrangements within the spirit and/or scope of the underlying inventive concept will become apparent to those skilled in the art from this disclosure.

Figure 1:
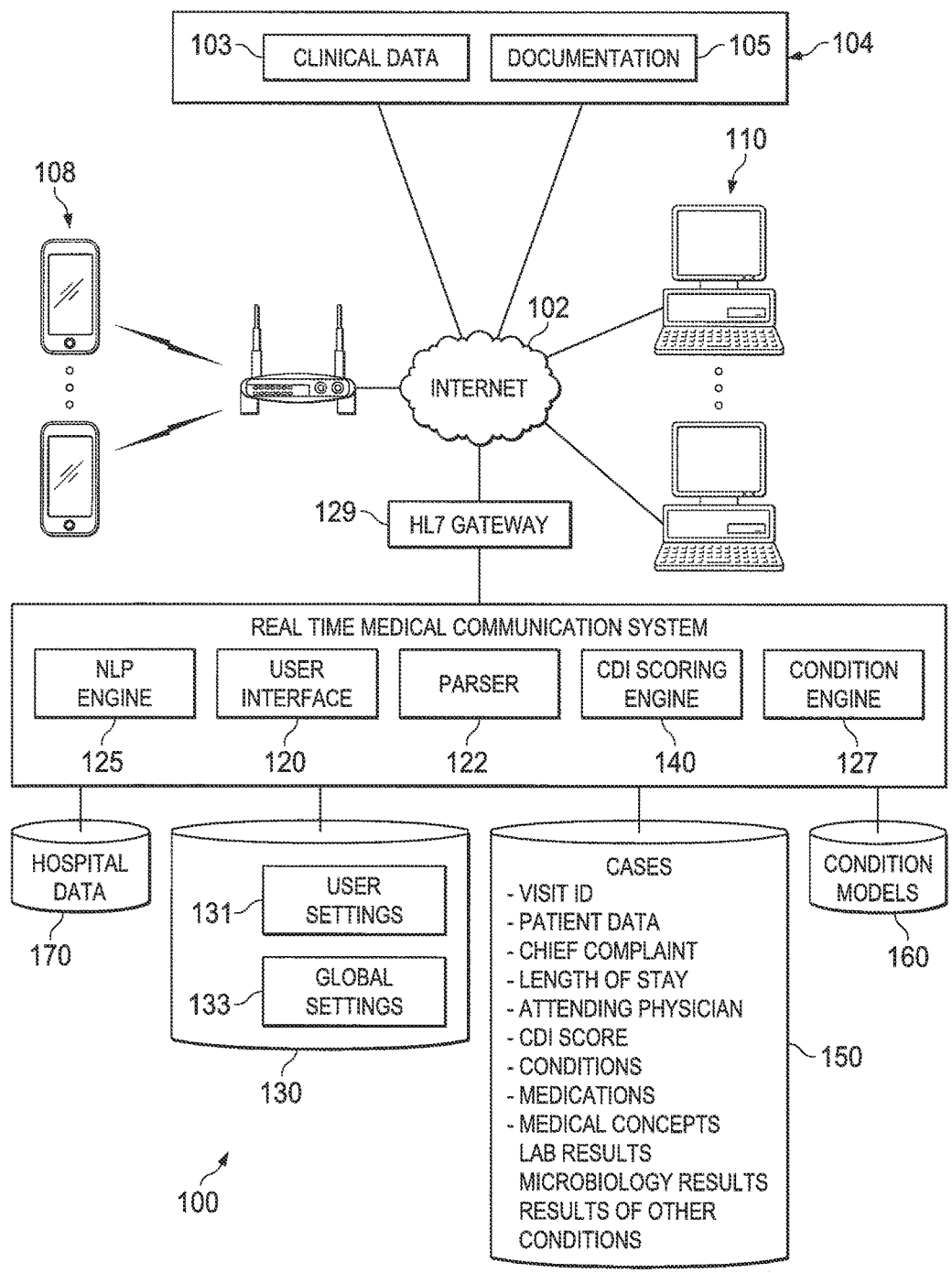
FIG. 1 depicts a diagrammatic representation of one example of a real-time medical communication system and associated network architecture for implementing embodiments disclosed herein.

FIG. 1 is a diagrammatic representation of one example of a real-time medical communication system and associated network architecture according to some embodiments. In the example illustrated, real-time medical communication system 100 is communicatively connected to hospital data source(s) 104 and various computing devices 108 . . . 110 over network 102 such as the Internet. System 100 may be embodied on a single or multiple server machine(s) and may include a plurality of system components including user interface 120, parser 122, condition engine 127, Natural Language Processing (NLP) engine 125, CDI scoring engine 140, and data store(s) storing hospital data 170, settings 130, patient cases 150, condition models 160, etc. Database management systems such as relational database management systems (RDBMS) and programming languages such as Structured Query Language (SQL) suitable for storing, accessing, and managing data communicated to and from as well as generated and/or used by system 100 are known to those skilled in the art and thus are not further described herein.

User interface 120 may represent an interface module configured for bi-directionally communicating with computing devices 108 . . . 110 via application level protocols suitable for web based applications, mobile applications, email applications, messaging (e.g., video, audio, text, etc.) applications, and so on, and for generating appropriate graphical user interfaces suitable for displaying on computing devices 108 . . . 110. Settings 130 may be received from any of computing devices 108 . . . 110 via user interface 120. Settings 130 may comprise user settings 131, referring to settings specific to one specific user of system 100, for example, a preference of a CDI specialist indicating a query score threshold for displaying CDI cases for review, or global settings 133, such as configuration parameters for condition models 160 or a system sensitivity rate reflecting the hospital's preferences with regard to false positives. In some cases, higher sensitivity (e.g., a greater likelihood of capturing query opportunities, but at an increased risk of false positives) may be desired, in other cases, a lowered sensitivity may be appropriate, as those skilled in the art can appreciate.

Parser 122 may be particularly configured for receiving and processing real-time medical/clinical data 103 and/or documentation 105 from hospital data source(s) 104 to identify entities of interest in the received data, extract them, and format/store them in appropriate data structures. Such entities of interest may represent features, factors, and/or medical concepts indicative of certain medical conditions. Additional details on hospital data source(s) 104 and parser 122 are provided below.

Documentation analysis begins with a process called Natural Language Processing (NLP). NLP refers to a process by which a computer reads text and extracts meaningful information from it. With physician documentation, NLP refers to identifying which medical concepts have been documented and what that documentation implies about those medical concepts (i.e., whether the documentation is stating that the patient does have a medical condition, does not have a medical condition, or may have a medical condition, etc.).

NLP engine 125 may be configured, according to some embodiments, for processing unstructured textual information (e.g., doctors' progress reports) contained in documentation 105 and, where applicable, hospital or clinical data 103. NLP engine 125 may operate to identify fundamental textual features or factors, such as instances of particular words, syntactical cues (e.g. certain words in the same sentence, etc.) which may then be inputted to parser 122 or machine learning systems to obtain a higher-level understanding of the text. NLP engine 125 may be any suitable NLP engine known in the art, such as Apache OpenNLP or NLTK 3.0.

According to some embodiments, condition engine 127 can be particularly configured for determining, based on all of the data associated with a patient's case, probabilities that: a.) the patient has a particular medical condition (such as, for example, hyponatremia), and b.) for each determined condition, the probability that the condition is accurately and/or correctly documented. Condition engine 127 can also be particularly configured for selecting which models (e.g., of models 160) to apply to the data associated with a particular case and application to generate these probabilities. Condition engine 127 may be implemented in hardware and/or software, or on a separate computer from other modules in the system.

CDI scoring engine 140 can be particularly configured for accessing one or more patient cases within cases 150 and evaluating such patient case(s) based on information currently available to system 100. The evaluation performed by CDI scoring engine 140 may comprise calling parser 122 to parse received real-time clinical data 103 and/or documentation 105 to determine entities of interest (e.g., features, factors, and/or medical concepts of certain medical condition(s)) in the received real-time medical data. Examples of real-time medical data are provided below.

CDI scoring engine 140 can also be particularly configured for calling condition engine 127 to determine which medical conditions are applicable to a particular patient case, given the entities extracted from the received real-time data. CDI scoring engine 140 may operate to call the data store of patient cases 150 to retrieve additional information and build a full data set (which includes the newly received real-time data) for the patient's current hospital visit.

Having assembled the full data set, CDI scoring engine 140 may operate to determine which condition models of condition models 160 are required for the determination of the patient's CDI score. For example, CDI scoring engine 140 may identify a diagnosis model and a documentation model for each condition for which the patient may have been diagnosed. This is further described in detail below.

CDI scoring engine 140 may run the determined condition models. Outputs from these condition models can be used to evaluate a patient case and generate a CDI score indicative of a CDI opportunity. In some embodiments, CDI scoring engine 140 may update CDI scores periodically, for instance, upon receipt of a time-based signal. The system-generated CDI scores may be stored as part of cases 150, and used by user interface 120 to generate an interface, based at least in part on the determined CDI scores, which provide a list of patient cases, prioritized by the determined CDI scores. CDI scoring engine 140 is further described in detail below.

Computing devices 108 may comprise mobile devices, such as cellular telephones, smartphones, tablet computers, personal digital assistants (PDAs), and the like, that run on various mobile operating systems such as iOS, Android, Windows Mobile, WebOS, BlackBerry OS, Palm OS, etc. Computing devices 110 may include wired computers such as desktop computers and/or wireless computers such as laptop computers that run on various operating systems such as OS X, Microsoft Windows, OpenVMS, VM, Solaris, and Linux, etc.

As a non-limiting example, each of computing devices 108 . . . 110 may include a central processing unit ("CPU"), read-only memory ("ROM"), random access memory ("RAM"), a hard drive ("HD") or any other types of non-transitory storage memory, and input/output ("I/O") device(s). The I/O devices can include a keyboard, monitor, printer, electronic pointing device (e.g., a mouse, trackball, stylus, touch pad or screen, digitizer, etc.), or the like.

As discussed above, system 100 may be embodied on a single or multiple server machine(s). Each such server machine may include CPU, ROM, RAM, HD, and I/O devices similar to those described above. Likewise, hospital data source(s) 104 may be one or more computing devices which include a CPU, ROM, RAM, HD, and I/O devices similar to those described above.

Although a single hospital data source 104 is shown in FIG. 1, skilled artisans appreciate that hospital data source 104 may represent a single source or multiple sources associated with a particular hospital system or healthcare facility. Furthermore, multiple hospital systems and/or healthcare facilities may be communicatively connected (via appropriate hardware, software, and network technologies) to system 100 and provide real-time medical data for use by system 100, including clinical documentation generated at a hospital.

As used herein, the term hospital refers to any healthcare facility, clinic, hospital, doctor's office, etc., and the term clinical documentation refers to healthcare information that documents a patient's condition and the care given to the patient. As will be further described below, real-time medical data from hospital data source 104 may be provided to system 100 via one or more feeds such as HL7 (Health Level 7) feeds. The HL7 feed may be provided to system 100 via an HL7 gateway 129. In some embodiments, HL7 gateway 129 may be integral to, or physically separate from system 100. The HL7 protocol is an open source protocol promulgated by Health Level Seven International, Ann Arbor, Mich., that defines how various healthcare facilities can communicate with each other. It is noted, however, that feeds via other protocols, such as the File Transfer Protocol (FTP) or Hypertext Transport Protocol (HTTP), are also possible.

Embodiments disclosed herein are capable of tapping into all available data streams. Example feeds may include, but are not limited to, admission-discharge-transfer (ADT) feeds (i.e., procedural or administrative information relating to each patient's stay at a facility); any orders (e.g., procedures/tests ordered for a specific patient); any lab results (e.g., from blood tests, etc.); any radiology results (e.g., results of x-rays, magnetic resonant imaging (MRI), computer-assisted tomography (CAT) scans, and the like); any results of cardiology exams; any prescriptions/pharmacy orders; any actual pharmaceutical/drug administration; any billing and coding data; and so on. Skilled artisans appreciate that HL7 ADT messages carry patient demographic information for HL7 communications, but also provide important information about trigger events (e.g., patient admissions, discharges, transfers, registrations, etc.). Segments in an ADT message may include a Patient Identification (PID) segment, a Patient Visit (PV1) segment, and occasionally an Insurance (IN1) segment. ADT messages are common in HL7 processing and are widely used in the healthcare field.

In some embodiments, system 100 may receive, at the minimum, ADT and lab results data feeds. Some data feeds can be optional. In some embodiments, system 100 may receive at least some of the following data feeds:

Lab Orders
Microbiology Results
Pathology Results
Pharmacy Orders
Radiology Orders
Radiology Results
Cardiology Results
Vital Signs
Physician Documentation In some embodiments, system 100 is always ready to receive these data feeds, 24 hours a day, seven days a week. In some embodiments using an HL7 feed, a stream of data may be updated when an event at a particular hospital or source is updated. As discussed above, the updated raw data may be stored in a hospital data database represented by hospital data 170 in FIG. 1. Parser 122 may parse the new information, and parse out entities of interest within clinical data 103, hospital data 170, and/or documentation 105.

In some embodiments, each piece of data is processed in near-real-time. As a specific example, most data can be processed within 10 minutes of receipt by system 100. Environmental and configuration settings can sometimes extend processing times. Each time a patient case receives new data, its CDI score is updated.

The CDI score can be a discrete numerical value representing a significance or level of opportunity for improvement for clinical documentation associated with a patient in a hospital. For example, a high CDI score may indicate that a patient has a medical condition that is reflected in their clinical data, but that is not correctly or accurately documented. A CDI score may be weighted by the significance (which may be expressed, for example, as a combination of clinical and financial concerns) of the under- or over-documented and/or over- or under-diagnosed patient medical condition. For instance, the system may determine that the clinical data of a particular patient admitted for treatment of sunburn reflects an undocumented dehydration (i.e., the documentation associated with the same patient does not contain dehydration as a documented condition). In some embodiments, the system may utilize a weighting scheme to ensure that the undocumented dehydration is a condition highly correlated to sunburn, as opposed to life-threatening sepsis, of which dehydration is also a condition.

CDI specialists have a finite amount of time and often cannot get to all initial reviews and re-reviews of patient charts for CDI purposes. Embodiments described herein can streamline a CDI specialist's task of determining which patient charts to review and enable them to make an informed decision as to how they could best improve the accuracy of the given clinical documentation. For example, a user interface 120 may operate to generate, in real-time, a list of patient cases prioritized by the determined CDI score. The prioritization provided by the system can enable them to focus on cases with the most impact when they perform CDI reviews, thereby improving the efficiency and effectiveness of their work. In turn, such an improvement could provide a positive impact on the hospital's insurance reimbursement rates, healthcare quality ranking, etc.

In some embodiments, the system may parse newly received real-time medical data concerning a patient and identify a body mass index (BMI) of the patient as an entity of interest. The system may determine (e.g., by consulting an indicator table storing indicator information vetted by subject matter experts) that the BMI for the patient is high and that a high BMI may be an indicator for obesity. The system may identify obesity as a medical concept associated with the patient's case and store this concept in the patient's case file in data store 150. The system may evaluate the patient's case, which now includes the newly determined medical concept, and determine that the current clinical documentation is missing information on obesity. Although the patient's attending physician(s) should have specified whether the patient is actually obese or overweight (if those labels apply), this documentation is commonly missed by physicians. The system can identify missing and/or inaccurate information in a patient's case and generate a CDI score such as a score of 0-100 that represents a significance or level of improvement. For example, a score of 100 may indicate that this patient's case is extremely likely to need a CDI review and the CDI review may result in a significant impact in improving the quality of the clinical documentation for this case.

By presenting a CDI specialist with a list of patient cases ranked according to the CDI score, the CDI specialist can easily prioritize which patient charts to review and when to initiate a query to resolve an under- or over-documentation issue. In some embodiments, input from a CDI specialist may also affect, both in the short term and in the long term, how the system scores patient cases for CDI specialist review.

(i) Short Term Impact—once a CDI specialist has reviewed a patient's chart and has taken the necessary steps to ensure that the clinical documentation for that patient is accurate (at the time the CDI review is complete), then, in some embodiments, the CDI score associated with the particular patient case can be updated to be (or reset to) zero for the time being. This CDI score may be updated again when new information about the patient's care is received and the patient's case is re-evaluated by the system, at which time, the system may generate a new CDI score indicating that a re-review may be needed for the patient's case to further improve clinical documentation on the patient's care.

(ii) Long Term Impact—a CDI specialist may indicate to the system (e.g., via a graphical user interface generated by user interface 120 of system 100) which queries resulted in actual improvement to clinical documentation. In this way, the system can learn and/or gain knowledge on what the global "success rate" of each query is relative to the CDI scoring process, and can globally adjust the weight of the CDI in the CDI scoring algorithm as needed.

Figure 2A:
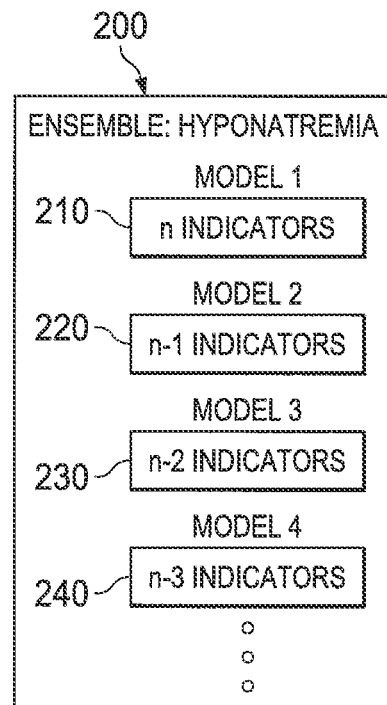
FIG. 2A depicts a diagrammatic representation of an ensemble of condition models according to some embodiments disclosed herein.
Figure 2B:
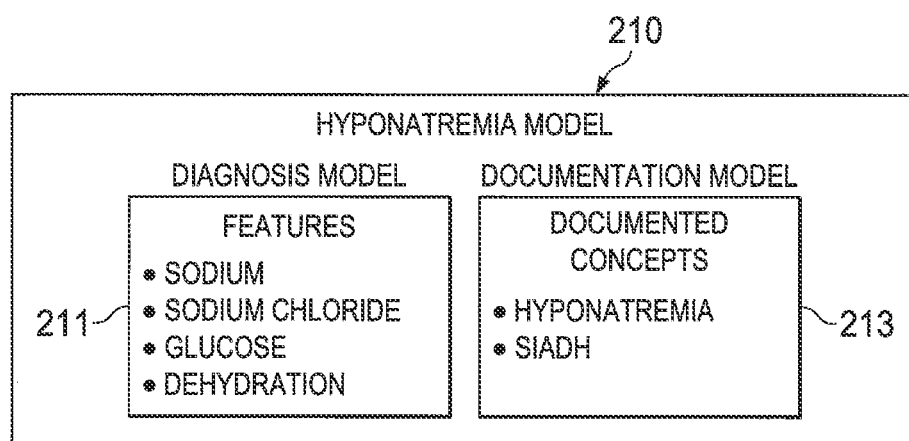
FIG. 2B depicts a diagrammatic representation of a condition model according to some embodiments disclosed herein.

Turning now to FIG. 2A, which depicts a diagrammatic representation of an ensemble of condition models according to some embodiments disclosed herein. In the example of FIG. 2A, an ensemble of condition models 210-240 for an example medical condition (hyponatremia) 200 is shown. As illustrated in FIG. 2B, there can be multiple types of condition models for each particular medical condition. Some embodiments of a system disclosed herein are particularly configured to process the following medical conditions:

Anemia
Heart Failure
Hyponatremia
Hypernatremia
Myocardial Infarction
Pancreatitis
Renal Failure (with the ability to distinguish between acute and chronic)
Respiratory Failure
Sepsis
Shock
Stroke As discussed above, each of these medical conditions has an ensemble of condition models. In embodiments, an ensemble may contain a number of condition models, with each condition model comprising a set of factors or indicators that are predictive of whether a particular medical condition is reflected in the received real-time clinical data (for a diagnosis model) or in the documentation (for a documentation model). In some embodiments, models 210-240 may leverage gradient boosted models, random forest models, neural network models, deep learning models or models based on linear regression. Other predictive machine learning models may also be utilized.

In some embodiments, condition models 210-240 may be ordered hierarchically based on factors considered by each, with a condition model considering the largest number of factors being the first choice (e.g., condition model 210 representing a condition model that is the best fit for a particular patient), followed by condition models (e.g., condition models 220-240) considering subsets of the factors considered by the first condition model. Condition models 220-240 can be considered as fallback alternatives to the first condition model in case of data scarcity. Accordingly, when a patient's sodium level, sodium chloride medication orders, glucose level, and dehydration data can be derived from the received real-time data, condition model 210 may be applied. As another example, when a patient's sodium level, sodium chloride medication orders, and dehydration data (but not glucose level) can be derived from the received real-time data, condition model 220 may be applied as that condition model is trained or best suited to consider these particular factors and thus would be the best fit for that particular patient. As a specific example, for a medical condition known as hyponatremia, condition model 210 may consider a set of factors indicative of whether a patient has hyponatremia, including the patient's sodium level, sodium chloride medication orders, glucose level, and dehydration. However, condition model 220 may exclude glucose as a factor and only consider a subset of those factors considered by condition model 210. Condition models 230 and 240 likewise may consider progressively smaller subsets of predictive factors for hyponatremia.

Skilled artisans appreciate that computer identification of medical conditions is a difficult proposition. Identification of even seemingly straightforward medical conditions like hyponatremia can be challenging because of nuance: small factors that, although independently may not be important, when taken together can materially impact diagnosis. Furthermore, highlighting a condition for CDI review adds additional complexity, as other not-strictly-diagnostic factors need to be considered. For example, a patient that shows an initial minor sign of renal failure (e.g., a slightly elevated creatinine level) might not be of interest for documentation review, but a patient with multiple or acute symptoms or a patient with persistent or worsening symptoms would be.

Because of this complexity, no prediction algorithm is perfect. However, according to embodiments, developing gradient-based models (GBMs) by means of a Machine Learning (ML) approach excels relative to other approaches for developing models for predicting the probability that a patient has a particular medical condition. In particular, the system can leverage ML algorithms to analyze large sets of data and learn how various combinations of factors yield results. In this way, the system can account for nuance and behavioral considerations much better than alternative approaches such as linear regression and strictly statistical methods. For example, ML models can be evaluated for each available medical condition supported by the system. Each per-condition ML model considers a multitude of individual factors drawn from orders, results, and basic patient information such as gender and age. The output of each per-condition ML model represents a "predictiveness factor"—the probability that the patient has the given medical condition. This predictiveness factor can be compared with a configurable threshold for the given medical condition such that if the predictiveness factor is not smaller than the threshold, the system considers the medical condition to be valid. This predictiveness factor does not directly impact CDI scoring described below, but in some embodiments may control whether or not a given medical condition is presented (e.g., via a user interface of the system) to a CDI specialist for a given patient case.

In some embodiments, per-condition ML models 210-240 may be developed by using a master set of coded hospital-provided data to train and test them. This master set may comprise hospital data collected, for instance, over an approximately three-month period, and may typically include data for hundreds of thousands of patient visits. Using interviews with experts, individual research, and high-level data analysis, an initial list of up to 150 potentially predictive factors, such as doctor's orders, lab results, and basic patient data (e.g., gender and age) can be compiled. For the purposes of developing and training the models, this master set is assumed to be correct in the aggregate, with patient medical conditions generally properly diagnosed (as reflected in the clinical data) and documented (as reflected in the documentation). Using a machine learning engine, including well known machine learning systems such as $H_2O.ai$ or GoLearn by Google, an ML analysis of some portion (for example, 75%, 80%, 90%, or 95%) of the master set of data can be conducted so that actually predictive factors can be identified from within the list of potentially predictive factors. The identified predictive factors may be ranked according to predictive value, and an ensemble of models considering a range of predictive factors from a minimum number of factors (e.g., condition model 240) to a full complement of predictive factors (e.g., condition model 210) may be constructed.

After an ensemble of condition models 210-240 is generated, they may be tuned and the predictiveness of the identified factors confirmed by testing the condition models against a second subset of the master set of hospital-provided data (for example, the remaining portion of the master set of data).

The training and testing process described above can be applied to various types of condition models. For example, as with a diagnostic per-condition ML model, factors considered by a per-condition documentation ML model may include medical concepts extracted by NLP engine 125 from received documentation concerning a particular patient. Specifically, NLP engine 125 can extract textual references to medical concepts from newly arrived documentation.

NLP engine 125 can examine received documentation and identify medical concepts in the documentation that may be predictive of the quality with which a medical condition is documented.

Skilled artisans will appreciate that there are many challenges to using NLP to understand clinical documentation. Such challenges include:

- Medical terms can be abbreviated, conjugated, or misspelled.
- The meaning of a term or phrase often depends on its location in a document (i.e., within a given paragraph or section) and the structure/organization of a document can vary widely, even within a single hospital.
- Layout conventions that are easy for a human to understand can prove difficult for a computer or may yield ambiguous results.

Embodiments may overcome these challenges by reducing the impact of NLP inaccuracy. Particularly, embodiments may apply ML in conjunction with NLP to identify patterns and combinations of larger sets of NLP results that may be predictive of documentation quality. Although any single NLP result (e.g., a documented medical concept) may not be accurate, multiple results representing the same, similar, or related medical concepts all considered together support a more comprehensive understanding of the document. The ensemble of condition models for each particular medical condition allows the system to adapt to documentation conventions that may vary from condition to condition. Some of the factors these documentation ML models consider include:

The number of times a medical concept has been mentioned in documentation.

The number of distinct ways a medical concept has been mentioned in documentation.

Which other related medical concepts have been mentioned in documentation.

In some embodiments, each time the system receives a new document for a patient, the document is run through the NLP engine and each of the documentation ML models to consider these factors. The NLP engine may operate to extract keywords (e.g., "acute renal failure"), determine counts of keywords, and determine syntactical relationships between identified words. All documented medical concepts that have been encountered for the patient thus far (i.e., from running NLP on both newly arrived documentation and from previous NLP runs from previously arrived documentation) are processed by per-condition documentation ML models. The output of each per-condition documentation ML model represents a "confidence factor"—the probability that the documentation received thus far positively documents a given condition.

Turning now to FIG. 2B, which provides a diagrammatic depiction of a condition model according to some embodiments disclosed herein. In the example illustrated in FIG. 2B, condition model 210 of medical condition 200 of FIG. 2A is shown. In this example, condition model 210 includes diagnostic model 211 and documentation model 213. Diagnostic model 211 takes as inputs entities and/or factors that have been found to be predictive of the probability that a medical condition is present in a particular patient case. In this case, diagnostic model 211 considers sodium levels, sodium chloride medication orders, glucose levels and indications of dehydration. Skilled artisans will appreciate that, depending on the condition and confidence level sought, condition models containing more or less predictive factors may be possible.

Documentation model 213 may contain textual medical concepts found to be predictive of the documentation quality for a particular medical condition. In this example, the NLP engine of the underlying system (e.g., NLP engine 125 of FIG. 1) may determine two medical concepts: hyponatremia and syndrome of inappropriate antidiuretic hormone secretion (SIADH), from the real-time documentation data (e.g., documentation 105 of FIG. 1).

In some embodiments, diagnosis model 211 and documentation model 213 may be used in conjunction to identify situations in which there is a significant difference or delta between the probability that a condition is present (or not present) and the probability that a condition is accurately (or not accurately) documented. Such situations may present CDI opportunities for CDI specialists. As a non-limiting example, one perspective on CDI can include initiating the following different types of queries:

Under-documentation queries. These may arise when the system identifies a medical condition that is not accurately documented. In such cases, the system may identify an opportunity for the CDI specialist to initiate a query to get the documentation clarified and/or augmented such that it appropriately accounts for the particular medical condition. This type of queries may be referred to as "impact," "quality," or "severity" queries.

"Over-documentation" queries. These may arise when the system identifies documentation for a medical condition, but cannot find the clinical evidence that supports that documentation. In such cases, the system may identify an opportunity for the CDI specialist to initiate a query to validate or correct the documentation such that the documentation correctly and accurately presents the medical condition(s) of the particular patient. This type of queries may be referred to as "clinical validation" queries.

In some embodiments, CDI scoring engine 140 may employ diagnosis model 211 and documentation model 213 to generate both an under-documentation score and an over-documentation score for each medical condition.

In some embodiments, an under-documentation score may represent a medical condition that is clinically valid and is not documented or sufficiently documented. The under-documentation score may be generated by calculating a condition predictiveness factor times the inverse of the documentation confidence factor. The predictiveness factor may be determined through application of a per-condition diagnostic ML model, such as diagnostic model 211. The documentation confidence factor may be determined through application of a per-condition documentation ML model, such as documentation model 213.

In some embodiments, an over-documentation score may represent a medical condition that is not clinically valid but is documented. The over-documentation score may be generated by calculating a documentation confidence factor (e.g., an output from documentation model 213) times the inverse of the condition predictiveness factor (e.g., an output from diagnostic model 211). These two scores are separately carried forward.

These special calculations are further described below with reference to FIGS. 1 and 3. In some embodiments, process 300 may be run continuously, triggered by an event (e.g., receipt of real-time data, a time-based signal, etc.), or applied on-demand. In some embodiments, process 300 may also be triggered in response to an event predetermined to be of particular relevance to the CDI analysis (e.g., surgery, transfer to the emergency room, receipt of new lab results, etc.).

Figure 3:
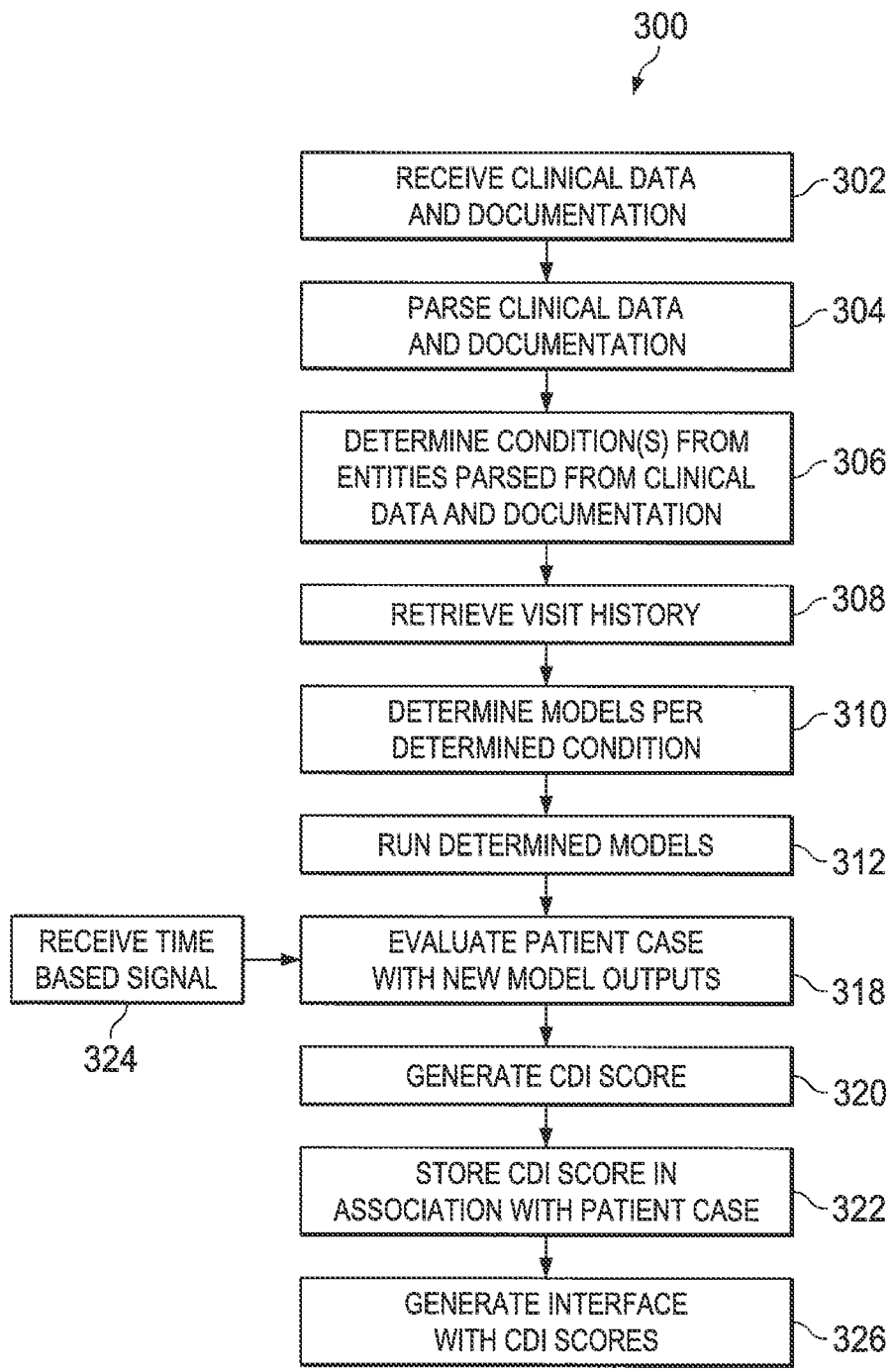
FIG. 3 is a flowchart illustrating one example of a method for large-scale data analysis and real-time medical communication according to some embodiments disclosed herein.

In the example of FIG. 3, process 300 may begin when real-time medical communication system 100 receives real-time medical data from data source(s) 104 (302). Depending upon factors such as the recency of the patient's admission, the real-time medical data received over a network by system 100 may comprise a patient's full visit record, or an update to an existing patient case. In some cases, real-time medical data for multiple patients may be received in a single transmission.

In some embodiments, real-time medical data may be received from various hospital or healthcare data sources 104. Such hospital feeds may be maintained and updated in real-time, for instance, when a new patient is admitted, a diagnosis is entered into the patient's chart, a procedure is performed on the patient, a drug is prescribed for the patient, a medicine is administered to the patient, a test is ordered for the patient, or a result from a lab test is received, etc. The received real-time medical data may be formatted as text messages (e.g., HL7 messages). System 100 may process the received HL7 messages into rows and columns and store same in cases data store 150.

An exemplary HL7 message is shown below. In particular, shown below is a sample HL7 message representing the results of a complete blood count (CBC) lab procedure:

---

MSH||^~\&|LAB|IODINE|||201606121531||ORU^R01|ID12345|P|2.3|||||PID|1|MRN12345|ACCT98765|1221|SMITH^BOB||19850608|M|||12345 MAIN ST^AUSTIN^TX^^78701|||||ACCT98765|123-45-6789||||||
PV1|1|I|FACILITY.1||||DRID12345^JOHNSON^SALLY||NONE^None|||||||N||REF||N||||||||||||||||CMC||FACILITY.1|||201606101110||||||

-continued

```
ORC|||||||||||||||||
OBR|1|ORDER123^LAB|ORDER123^LAB^ALTORDER5678|
CBC^LABCBC|||201606111212||||||201606111244||
DRID12345^JOHNSON^SALLY||||||||LAB|F|^^^^^R|||||||
OBX|1|ST|WBC^WBC^L|8.7|K/uL|3.6-10.8|N||F|||201606111244||
OBX|2|ST|RBC^LAB RBC^L|1|4.83|M/uL|4.2-
5.4|N|A^S|F|||201606111244||
OBX|3|ST|HGB^Hemoglobin^L|1|13.6|g/dL|12.0-
16.0|N||A^S|F|||201606111244||
OBX|4|ST|HCT^Hematocrit^L|1|40.7|%|37-47|N||A^S|F|||
201606111244||
OBX|5||ST|PLT^Platelet Count^L|1|390|K/uL|150-
400|N||A^S|F|||201606111244||
OBX|6|ST|MPV^MPV^L|1|10.2|fL|7.4-10.4|N||A^S|F|||
201606111244||
OBX|7|ST|GRP^Gran % (Auto)^L|1|74.7|%|42-
72|H||A^S|F|||201606111244||
OBX|8|ST|LYP^Lymph % (Auto)^L|1|18.9|%|20.5-
51.1|L||A^S|F|||201606111244||
OBX|9|ST|MIDP^Mid Range %
(Auto)^L|1|6.4|%||N||A^S|F|||201606111244||
OBX|10|ST|GRA^Gran # (Auto)^L|1|6.5|K/uL|1.8-
7.7|N||A^S|F|||201606111244||
OBX|11|ST|LYA^Lymph # (Auto)^L|1|1.6|K/uL|1.0-
4.8|N||A^S|F|||201606111244||
OBX|12|ST|MIDA^Mid Range #
(Auto)^L|1|0.6|K/uL||N||A^S|F|||201606111244
```

The first line—the MSH segment—indicates that this is a result (as indicated by "ORU-R01").

The 2nd line—the PID (patient identifier) segment—provides identifying information about the patient. In this example, the patient's name is Bob Smith; he lives at 12345 Main St.; his medical record number is MRN12345; and his account (case) number is ACCT98765.

The 3rd line—the PV1 (patient visit) segment—provides status information about the patient's current visit. In this example, the message segment indicates that he is an inpatient who was admitted on Jun. 10, 2016 at 11:10 a.m.

The 4th line—the OBR segment—provides information about the order that was previously placed that caused this lab procedure to be performed. In this example, the message segment indicates that Dr. Sally Johnson ordered the procedure with id "CBC" and named "LAB CBC" at 12:12 p.m. on Jun. 11, 2016.

Each of the remaining lines contains a single result. For example:
OBX|1|ST|WBC^WBC^L|8.7|K/uL|3.6-
10.8|N||F|||2016061101244||
OBX=indicates that this line contains a result
1=indicates that this is the first result line returned for the order
ST=indicates that the result contains a simple string value
WBC^WBC LAB^L=indicates that the result is a "WBC LAB" result with an ID of "WBC"
8.7=This is the actual numerical result
K/uL=These are the units of measure for the result
3.6-10.8=This is the reference range for this particular result
N=This is where abnormality flags would be. N indicates "normal"
F=Final status
201606111244=Observation occurred at 12:44 p.m. on Jun. 11, 2016

In some embodiments, this exemplary HL7 message may be processed by HL7 Gateway 129 or another module within real-time medical communication system 100, to translate the raw data feed into structured data (e.g., a plurality of rows) which may then be added to a table designated for storing lab results (e.g., a "LabResult" table) in cases data store 150. In this case, the "LabResult" table represents a table associated with a particular data type.

In some embodiments, the formatted real-time medical data may include clinical data 103 and documentation 105, as discussed above. Clinical data 103 may be parsed by parser 122 (e.g., responsive to a call from CDI scoring engine 140) to extract entities, objects or concepts (collectively referred to herein as "entities") of interest or a modification to an existing entity (304). An entity of interest may represent a new patient, case, caregiver (e.g., an attending physician, a nurse assigned to the patient, a nurse assigned to the floor where the patient is located, etc.), diagnosis, procedure, order, drug, lab result, the patient's location in the hospital (e.g., whether or not a patient is in the Intensive Care Unit), the patient's payer (e.g., whether the payer is Medicare, an insurance company, or if the patient is uninsured), the patient's length of stay (in many cases, query opportunities may decrease after a patient's stay length exceeds a certain threshold), data indicating special situations (e.g., surgery, palliative care), and whether a patient's case has already been reviewed, as hospital policies may favor early review of cases, etc.

As an example, if an entity of interest indicates that a new attending physician has appeared in the medical data received about a particular patient, parser 122 may extract the entity of interest and create a new database entry for storing information about the attending physician. As described above, in the context of this disclosure, entities of interest may particularly include entities representative of factors, features, and/or medical concepts indicative of certain medical conditions.

Extraction of entities may be governed by global settings 131 and configurable via user settings 133. For example, pertaining to the "LabResult" table discussed above, when parser 122 processes rows of data associated with the "LabResult" table, it would extract or update (if necessary) an entity for the attending physician referenced, and could create one or more pieces of information from the various OBX lines. The entity created or updated in this example can be an "attending physician" who has been newly identified as "Sally Johnson." In such cases, the system may:
  search an attending physician in database 150 with an identifier "DRID12345";
  create an entry for this attending physician if "DRID12345" does not exist;
  set the first name to "SALLY" and the last name to "JOHNSON," and
  save the entry with information for the new attending physician in database 150.

Incoming documentation 105 may be parsed in the same or analogous manner. In such cases, however, parser 122 may operate in conjunction with NLP engine 125, with NLP engine 125 extracting, for instance, documented diagnoses and/or medical concepts within the text of received documents 105, and with parser 122 reviewing the output of NLP engine 125 at a higher level of extraction to recognize entities of interest in documentation 105.

In some embodiments, certain entities of interest extracted by parser 122 (e.g., entities representing features, factors, and/or medical concepts associated with certain medical conditions) may be provided as inputs to condition engine 127. This may be done, for instance, by CDI scoring engine 140 calling condition engine 127 with outputs from parser 122. Condition engine 127 may operate to determine one or more medical conditions that may be present in clinical data 103 and/or documentation 105 based on features, factors, and/or medical concepts found in clinical data 103 and/or documentation 105 (306).

For example, based on presence of a patient's sodium level, sodium chloride medication orders, and a note of dehydration in clinical data 103 and/or of the presence of the word "hyponatremia" (i.e., a documented medical concept) in documentation 105, condition engine 127 may determine a medical condition "hyponatremia" for further analysis. Skilled artisans appreciate that, while process 300 is described using a medical condition for a patient as an example, the real-time medical data received from data source(s) 104 may indicate multiple potential medical conditions for that patient and/or for multiple patients. If nothing in the received real-time medical data indicates a potential medical condition worthy of further investigation, process 300 may terminate and/or loop back to wait for the next batch of real-time medical data. For the purpose of illustration, in this example, condition engine 127 has determined that, based on feature(s) and/or medical concept(s) found by parser 122 in clinical data 103 and/or documentation 105, a medical condition known to condition engine 127 as "hyponatremia" should be further analyzed for CDI potentials.

To fully analyze the determined medical condition, CDI scoring engine 140 may operate to retrieve the current knowledge of a particular patient visit (e.g., from admission to present time) from cases data store 150 and build a full data set of that patient's visit (308). Cases data store 150 is continuously updated with real-time medical data, so each patient case stored therein is up-to-date until the next communication with data source(s) 104 occurs.

As a non-limiting example, a full data set thus built for a patient visit may include, but is not limited to: a visit ID, patient data (e.g., height, weight, other pertinent patient attributes, etc.), the patient's chief complaint (e.g., fatigue, lightheadedness, pain, etc.), the identity of the patient's attending physician, any previously determined CDI scores, any determined and/or documented medical conditions, any medications, any diagnosis/medical concepts/features parsed from clinical data 103 and visit documentation 105, any lab results, any microbiological analysis results, and any results of other conditions associated with the patient, and so on.

In some embodiments, CDI scoring engine 140 may determine a difference, or "delta" between medical information most recently extracted for a patient visit and medical information already exists in cases data store 150 for the same patient visit. This determination of the "delta" may comprise: a.) determining one or more entities for which there may be a change in a value (e.g., a new blood pressure reading or a different glucose level), changes for which the newly received medical data creates (e.g., a new patient admission and hence a new patient visit is to be created in cases data store 150), or changes for which a category of data is to be created and/or updated (e.g., the entity representing a feature "blood sodium level" was not previously present but is found in the newly received real-time medical data). This determination may take several forms, and may include mapping the categories of entities and entity values previously identified in connection with a case to identify areas of change.

By way of example, suppose that sodium and glucose levels are already part a patient's visit. Newly received medical data indicates that the same patient's sodium levels have not changed, but the glucose levels are elevated and "dehydration" (which is a factor for the medical condition "hyponatremia") is noted in the clinical data. CDI scoring engine 140 may determine what diagnosis model and documentation model should apply to the determined medical condition "hyponatremia" based on this delta (310). Briefly referring to FIG. 2A, suppose that the most data-scarce model 240 for hyponatremia requires the presence of at least three indicators: sodium levels, glucose levels, and dehydration. Based on the changes in the categories of entities in the patient's case, CDI scoring engine 140 may determine that the most data-scarce model 240 is to be applied for hyponatremia. This selection process is performed for both a diagnosis model and a documentation model for each medical condition. For example, suppose "hyponatremia" was not previously documented in a patient visit, but is found as a documented medical concept in the newly received documentation 105. CDI scoring engine 140 may, based on this delta, determine that documentation model 213 is to be applied. In some embodiments, this determination may be made to select the most data-rich or multivariate model in an ensemble of condition models, as described above.

In some embodiments, once diagnosis and documentation models most appropriate for a particular medical condition are determined based on the richness of data in a patient's visit, process 300 may proceed to run these models (312). The outputs from the diagnosis and documentation models may comprise numerical probabilities (which may each be expressed as a number between 0 and 1) corresponding to condition-specific factors determined from application of the diagnostic and documentation models associated with the particular medical condition.

Following the example above, inputting values of the patient's sodium level, sodium chloride medication orders, glucose level, and indication of dehydration to diagnosis model 211 may result in a numerical value of 0.60, representing a determination that there exists a 60% probability that the patient has hyponatremia. Similarly, applying the documented medical concepts parsed from the documentation associated with the patient's visit to documentation model 213 may result in a value of 0.30, representing a 30% probability that hyponatremia has been accurately documented in the patient's visit. Such outputs from the diagnostic and documentation models may be stored in a cache, sent directly to CDI scoring engine 140, stored in cases data store 150 or any other suitable non-transitory memory. At this time, these two probabilities are carried forward separately (i.e., they are not combined in any way just yet).

Skilled artisans will appreciate that model sensitivities and confidence levels are configurable. Furthermore, additional factors may be included. For instance, it may be the case that, given the same indications of dehydration, glucose and sodium numbers, but also data showing the administration of salt tablets, diagnosis model 211 might return a value of 0.80, indicating an 80% probability that the patient has hyponatremia.

In some embodiments, model sensitivities and confidence levels may be adjusted or otherwise configured via settings 130, for instance, by changing or adding thresholds to settings 130. Such thresholds may be representative of the overall magnitude of the difference between the diagnostic and documentation probabilities required for further evaluation and computation. For instance, if, for hyponatremia, the models return a diagnostic probability of 0.95 and a documentation probability of 0.89, the 0.06 difference may fall below the threshold value for potential CDI opportunity worthy of further exploration (e.g., the possibility of over- or under-documentation for this particular medical condition). In this example, the high probability that hyponatremia is present in the clinical data and correctly documented in the documentation make it a very poor CDI candidate, and the precise CDI presented by this condition is sufficiently close to zero as to not be worth computing. As another example, if the diagnostic probability for a medication condition is 0.95, but the documentation probability for the same medication condition is 0.15, the 0.80 difference in the two probabilities indicates that this medication condition likely presents a CDI worth further analysis. Skilled artisans will appreciate that adjustment of these threshold values may affect both the sensitivity of the system and the incidence of "false positives." Depending on the user's preferences, a higher or lower sensitivity may be desirable.

In some embodiments, each of the per-condition ML models (the condition prediction and documentation analysis models) has a configurable sensitivity setting, providing Low, Medium, and High levels of sensitivity. In some embodiments, the system may be configured to use the level of sensitivity that maximizes that number of positive identifications while staying below a 1.0% false positive rate. The sensitivity of a particular per-condition ML model can be increased to capture more opportunities, but at the expense of also increasing the false-positive rate for that per-condition ML model.

With these outputs, CDI scoring engine 140 may operate to evaluate a patient case (318). As described above, this evaluation can be triggered in many ways, including via a time-based signal indicating a need to initiate a CDI determination on a patient's case (324). As further explained below, CDI scoring engine 140 may operate to generate a CDI score for a particular patient visit, the CDI score indicative of the potential of CDI for this particular patient visit (320). The generated CDI score is stored in association with the patient case in cases data store 150 (322) and can be used to generate a graphical user interface (e.g., by interface module 120 of FIG. 1).

FIG. 4 depicts a diagrammatic representation of one example of graphical user interface (GUI) 400 of a high fidelity CDI smart scoring system disclosed herein (e.g., system 100 of FIG. 1), showing example patient cases prioritized based on their corresponding CDI scores generated by a CDI scoring engine of the system (e.g., CDI scoring engine 140 of FIG. 1). GUI 400 may be suitably configured for running on various types of network-enabled computing devices, including handheld devices, smart phones, laptops, desktop computers, etc. As shown in FIG. 4, GUI 400 can be particularly configured for a CDI specialist to perform a CDI review and may include contextual information that explains why a patient may be scored unusually high or low, thereby giving the CDI specialist a data-science driven explanation relative to the accuracy of the outcome from the CDI scoring process. Examples of contextual information shown in FIG. 4 are described below.

In FIG. 4, a list of patients 402 is provided and categorized into different groups, including priority cases 432 and low priority cases 434, etc. The priorities of these cases, in this example, are ranked based on their current corresponding CDI scores which, as described above, are generated based at least in part on the medical data received in real-time over a network from data source(s) 104. Contextual information for each patient case may be shown in columns 404, 406, 408, 410, 412, 414, etc., representing a location of the patient, a payer for the patient, any potential medical conditions that need to be reviewed, any outstanding query, the patient's length of stay ("LOS") and geometric mean length of stay ("GMLOS") information, review status, etc.

As a specific example, patient case 416 may be shown on GUI 400 as having CDI scale 418 representative of a corresponding CDI score. As discussed above, the higher a CDI score is, the higher the possibility of CDI opportunity exists in a patient case. Here, three dots out of four on CDI scale 418 signals to the CDI specialist that patient case 416 has a high potential for CDI, as compared to other patient cases in priority cases 432. The CDI specialist can quickly scan specific location 420 and payer 422 associated with patient case 416, which may facilitate the CDI specialist in determining whether to further review patient case 416 for CDI. Skilled artisans appreciate that the payer information (or the lack thereof) may be germane to the CDI specialist's decision as to whether or not to pursue to a query.

Following the above example, GUI 400 may show that the high CDI priority of patient case 416 is due to a potential medical condition "Hyponatremia" 424. As illustrated in FIG. 4, conditions 408 are shown in GUI 400 as special indicators "S." In this case, special indicator 424 signals to the CDI specialist that the high fidelity CDI smart scoring system has determined that there is a high probability that patient case 416 has inconsistent, incomplete, and/or incorrect data, for instance, a medical condition that is under-documented (e.g., supported by clinical data 103 but not documentation 105) or over-documented (e.g., documented in documentation 105 but not supported by clinical data 103). In some embodiments, one or more of the following types of custom indicators may be supported:

Special Indicators—Custom special indicators can be configured to encourage/force prioritization of patient cases that experience significant events.

Figure 5A:
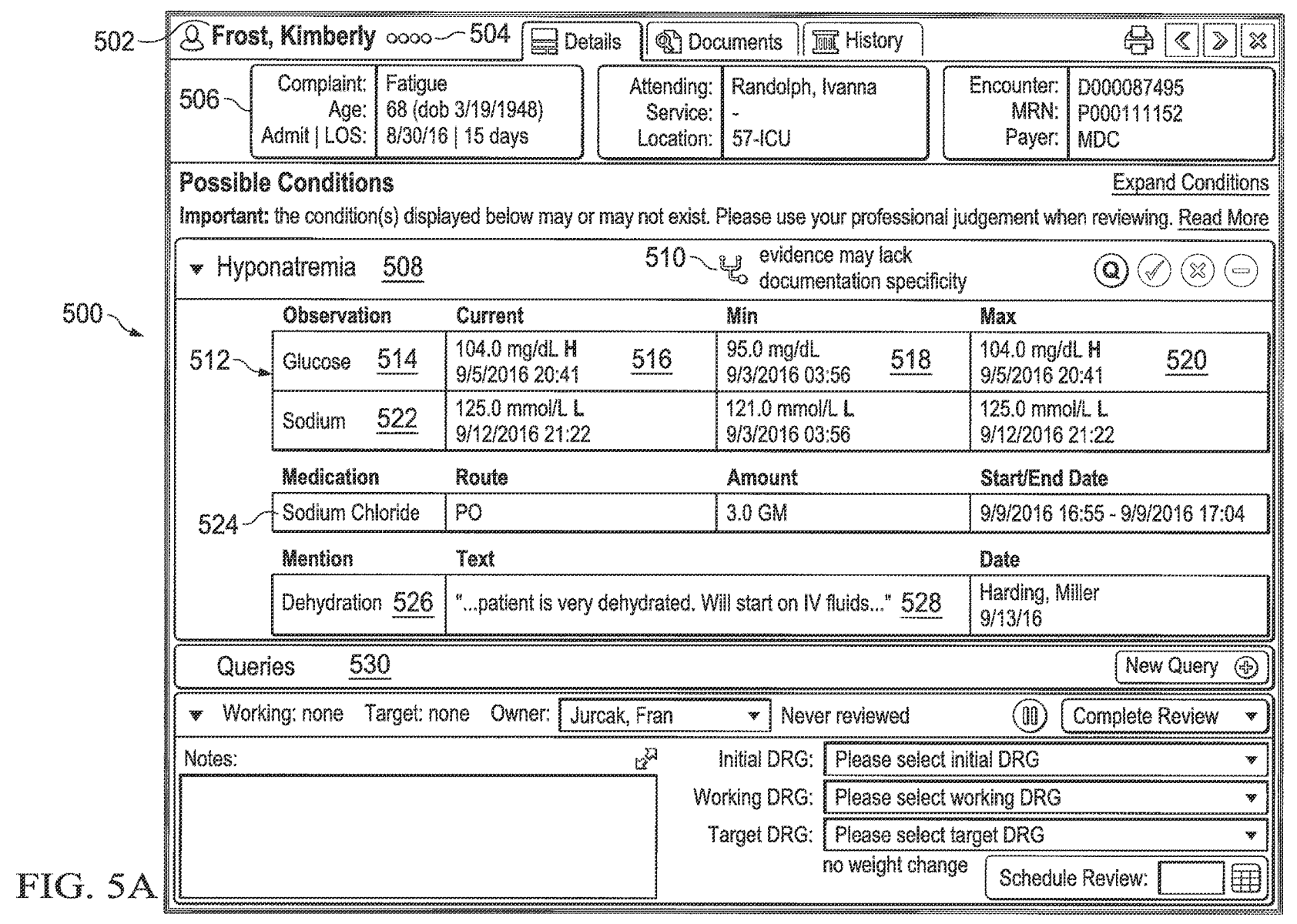

Other Indicators—An uncategorized indicator that is shown in, for instance, in a section of a patient details view (see e.g., FIG. 5A). This type of indicators does not impact CDI scoring, but can be useful to provide additional information to users.

Additional Condition Indicators—Similar to a custom "other" indicator, but is rendered inside the condition section of a GUI if the system predicts that the condition exists. If the system does not predict the condition, the indicator may be shown in a section of a patient details view. This type of indicators does not impact CDI scoring, but can be useful to provide additional information to users.

Custom indicators can be configured to prevent particular medical conditions from being displayed unless both the ML model predicts that the medical condition exists and the indicator triggers. This allows for an additional level of control for CDI programs that may have stringent rules for submitting queries on certain medical conditions. For example, a hospital may not want medical condition ABC considered unless medical condition XYZ has happened.

As described above, each condition prediction ML model processes a number of "factors" that ultimately drive the output of the model. In some embodiments, some or all of these factors may be displayed in a patient's details view. In some embodiments, the system may provide the ability to modify which factors are shown. For example, factors can be hidden from the user interface but still be used in the ML model. Furthermore, additional factors can be added to the user interface but will not be used as inputs to the ML model.

As illustrated in FIG. 4, GUI 400 may also show query status 410, LOS/GMLOS 412, and review status 414 for patient case 416. Query status 410 which has a "nil" value for patient case 416 indicates that no query has been initiated or outstanding in patient case 416. LOS/GMLOS 412 which has a "9d/-" value 428 shows that this patient has spent 9 days at location 420. As discussed in greater detail herein, LOS may be a factor considered in a CDI scoring process—a patient case's CDI score may decrease as LOS increases. In the example of FIG. 4, review status 414 which has a "Never" value 430 shows that, during this 9-day visit, patient case 416 has so far not been reviewed for CDI. Note that when a patient case has been queried and/or reviewed, it may be removed from a priority list for a predetermined interval (e.g., 24 hours), unless a new event has occurred. This period is referred to as a "quiet time." Skilled artisans appreciated that each piece of information shown in GUI 400 may be user-selectable so that the CDI specialist can "drill down" for further information. Skilled artisans also appreciate that GUI 400 may be configured to show more or less information relative to each patient case. Thus, GUI 400 is meant to representative and non-limiting.

Turning now to FIG. 5A, which depicts a diagrammatic representation of another example of a graphical user interface of a high fidelity CDI smart scoring system disclosed herein. In this example, GUI 500 may be generated (for instance, by interface module 120 of system 100 shown in FIG. 1) in real time, responsive to a CDI specialist selecting patient case 416 of GUI 400 shown in FIG. 4 for CDI review.

In the example of FIG. 5A, GUI 500 shows patient name 502 (which corresponds to patient case 416 shown in GUI 400 of FIG. 4) with associated priority on CDI scale 504 (which corresponds to CDI scale 418 shown in GUI 400 of FIG. 4) and several tabs to different pages of information, including "Details," "Documents," and "History." In the "Details" page, possible medical conditions for patient 502 are shown, including hyponatremia 508. Notice that GUI 500 also shows, via admission section 506, the reason why patient 502 was admitted. In this case, patient 502 was admitted for "fatigue." However, the high fidelity CDI smart scoring system has determined that there exists a meaningful probability that hyponatremia 508 is not accurately reflected in, for instance, the documentation associated with the patient case. This is noted on GUI 500 via note 510.

GUI 500 further provides data and documentary evidence supporting the determination of hyponatremia 508 being a possible, undocumented (or under-documented) medical condition for patient 502. Referring to FIG. 2B, GUI 500 may present the values for one or more of the predictive factors considered by diagnostic model 211 associated with the particular medical condition hyponatremia. In this example, these values are presented via "Observation," "Medication," and "Mention" sections. These sections contain information parsed from real-time medical data received from data source(s) 104. For example, the "Observation" section may show the patient's current, minimum, and maximum glucose measurements 514 in entries 516, 518, and 520. These entries represent data points that are fed into diagnostic model 211 for the particular medical condition hyponatremia. Additional data points may include sodium chloride 524, shown in the "Medication" section, and an indication that dehydration 526 was mentioned in the received real-time clinical data. Textual evidence 528 supporting the indication of dehydration is shown in the "Mention" section of GUI 500 as well. GUI may additionally include buttons, icons, and/or other interface elements 530 associated with various functions of the underlying system, for instance, initiating a query for the patient case under CDI review.

Figure 5B:
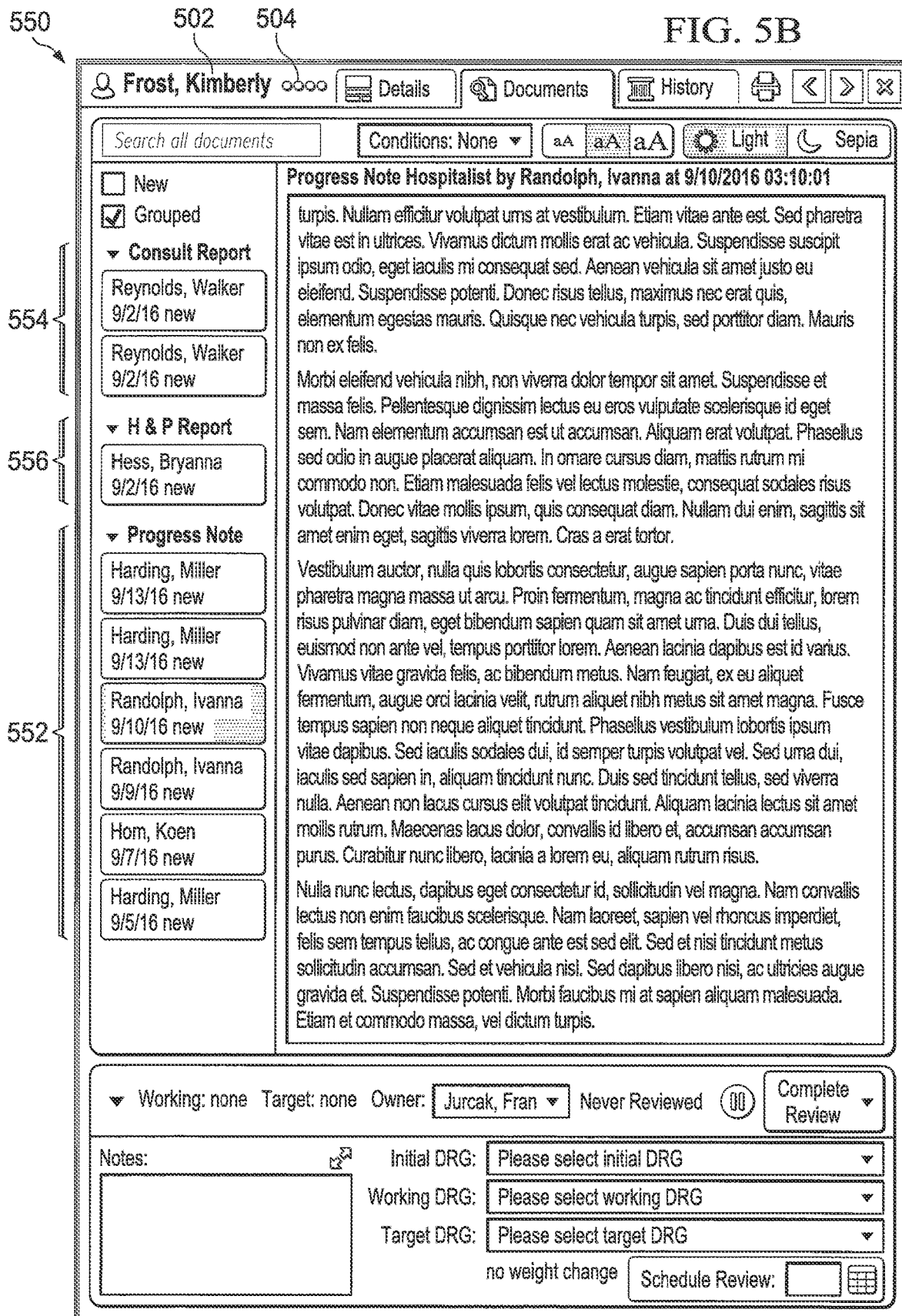
FIG. 5B depicts a diagrammatic representation of another example of a graphical user interface showing documentation for a patient's visit according to some embodiments disclosed herein.

The "Documents" page for patient 502 is shown via GUI 550 of FIG. 5B. As illustrated in FIG. 5B, GUI 550 may be particularly configured to provide the CDI specialist with access to view documents associated with patient 502, including any consultation reports 552, any health and physical ("H &P") reports 554, and any progress notes 552.

In some embodiments, documents may be arranged or otherwise presented on GUI 550 to provide the CDI specialist with an effective visualization of the documented status of patient 502. For example, the documents may be grouped by category and/or arranged in a chronological order. Other presentation styles/arrangements of interactive user interface elements are also possible, as skilled artisans can appreciate. Responsive to the CDI specialist selecting an interactive user interface element such as an icon or a button corresponding to a particular document, the content (e.g., in full text form) of that document may be automatically retrieved from a stored location (e.g., in cases data store 150) and shown in a separate section, frame, or window.

Figure 6:
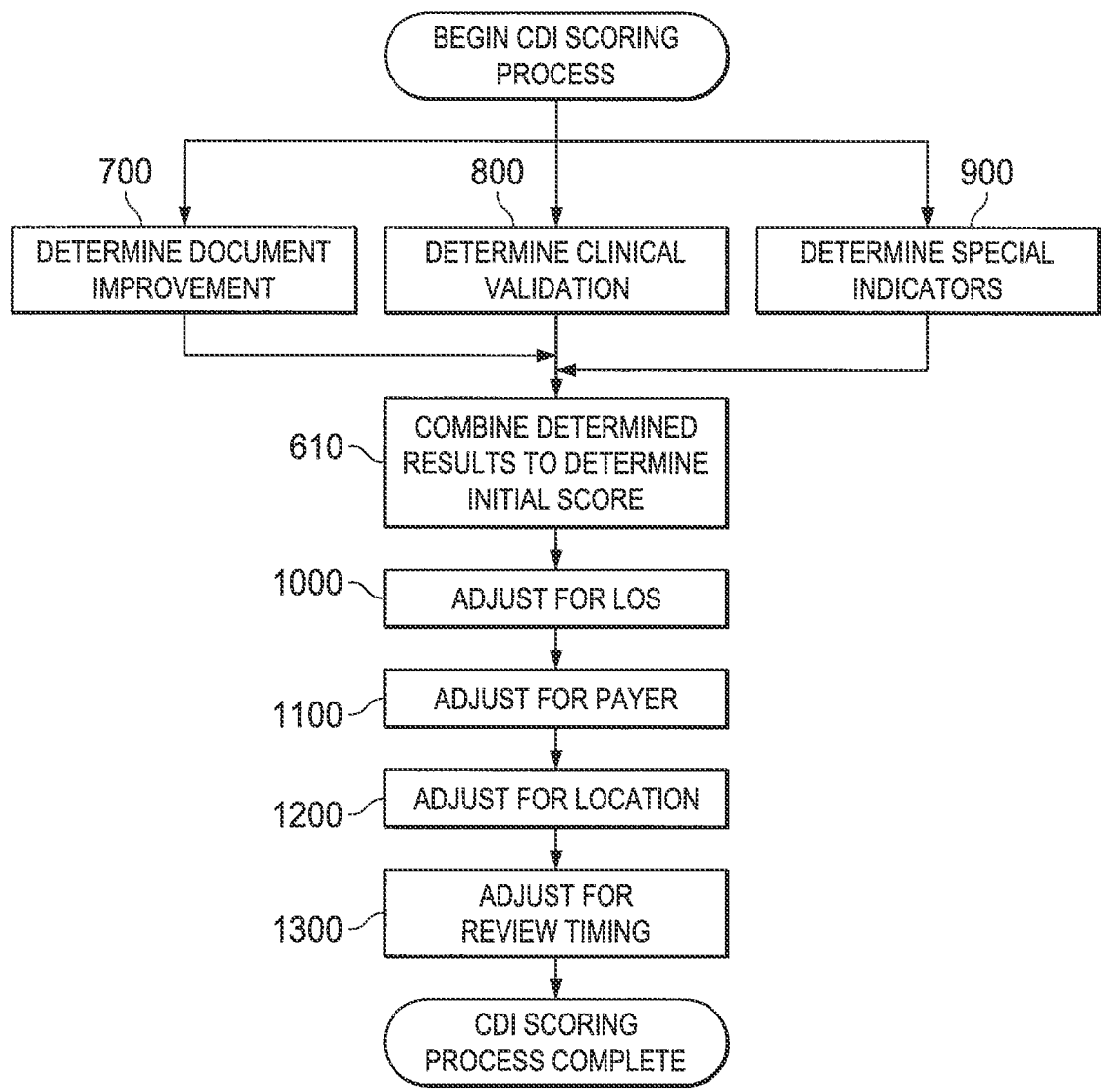
FIG. 6 is a flowchart illustrating one example of a CDI scoring method according to some embodiments disclosed herein.

FIG. 6 is a flowchart illustrating one example of a CDI scoring method according to some embodiments disclosed herein.

Characteristics of the CDI scoring method may, in some cases, include balancing between magnitude of potential change and proximity to discharge—a patient with a smaller opportunity but close to discharge may be a higher priority for review than a larger opportunity that was just admitted; factoring in the value of reviewing the case while it is still active before the patient leaves the facility and before the doctor's focus shifts to new cases; favoring new information—a patient with an overall higher value case but for whom all the information was present at the last review will score lower than a patient with a smaller opportunity but for whom some of the information is new (e.g., new alerts); understanding that re-reviewing a case with no new information is less likely to discover an opportunity than reviewing a case with new information; and overestimating rather than underestimating an opportunity (because clinical documentation as given tends to be imperfect). For example, if received medical data contains evidence of a kidney infection (with a relative weight of 0.78) and septicemia (with a relative weight of 1.10), septicemia is used as the basis. As another example, if data for documenting BMI as a comorbidity is missing or insufficient, the CDI scoring method may err on the side of assuming it is undocumented (missing), rather than assuming it is documented.

When evaluating a particular patient case represents, example factors considered by a CDI scoring method may include:

What is wrong with the patient

What secondary conditions (comorbidities and complications) are exacerbating the patient's primary condition How good is the attending physician for the case (or are physicians in general) at correctly documenting the conditions associated with this patient Is the patient in a hospital location such as the intensive care unit (ICU) or telemetry that hints at greater severity for that patient Who is the payer for the patient and how much do they pay relative to payers for other patient cases How much has happened to the patient since the last review Is the patient close to discharge (because it would be easier to correct the documentation prior to discharge)

As illustrated in FIG. 6, CDI scoring process 600 may include sub-processes 700, 800, and 900. Process 700 implements a method for determining a probability (referred to herein as a document improvement score or under-documentation score) that a potential medical condition found present in the clinical data of a patient case is not accurately documented or is missing from the documentation associated with the patient case. In process 700, the individual under-documentation scores are evaluated (e.g., using diagnosis model 211 of FIG. 2 in conjunction with queryability factors in some embodiments) to yield an overall under-documentation score. Queryability factors, also referred to as query opportunity scores, represent additional considerations that may be applied. For example, if the patient case was previously reviewed, the impact of data received prior to the review may be discounted. As another example, if any conditions have been queried, their under-documentation scores may be zeroed. Furthermore, if a query is performed and the documentation improved, the CDI score may be adjusted for the impact on the quality of documentation. Optionally, the under-documentation score may optionally be adjusted for effort. Process 700 is further described below with reference to FIG. 7.

Process 800 implements a method for determining a probability (referred to herein as a clinical validation score or over-documentation score) that a medical concept documented in a patient case is not valid or is not supported by the clinical data associated with the patient case. In process 800, over-documentation scores can be statistically aggregated across all medical conditions on the patient case, yielding an overall over-documentation score. Process 800 is further described below with reference to FIG. 8.

Process 900 implements a method for statistically accumulating any special indicators that have triggered for the patient case to yield a separate special indicator score. These special indicators are not necessarily tied to any particular medical condition. In some embodiments, the greater of the special indicator score and the query opportunity score is carried forward for further processing. This is further described below.

The numerical results (e.g., under-documentation scores, over-documentation scores, and the greater of the special indicator score and the query opportunity score) from sub-processes 700, 800, and 900 are combined to produce an initial CDI score (610). This single number captures the overall priority of a patient case, representing the overall likelihood that if a CDI specialist reviews the patient case, they will find that the documentation for the patient case can be improved.

Depending upon predetermined settings (e.g., at the request of a hospital), the CDI score may be further adjusted via additional processes for patient location, payer, post-admit "quiet period," post-review "quiet period," etc. Example sub-processes 1000, 1100, 1200, and 1300 are further described below with reference to FIGS. 10, 11, 12 and 13, respectively.

CDI scores thus generated for patient cases by CDI scoring process 600 can be used to identify patient cases that have the highest potential for generating additional reimbursement from payer(s). For example, a high CDI score may indicate to a CDI specialist an opportunity to query an attending physician as to whether an undocumented medical condition should be documented or whether the severity of a documented medical condition should be elevated to be consistent with evidence found in the clinical data for the same patient case. CDI scores can be stored (e.g., in cases data store 150 of system 100 shown in FIG. 1) and updated as more information is received. As a result, the patient cases can be continuously prioritized for CDI review based on the most up-to-date medical data from data source(s) 104.

The final CDI score from CDI scoring process 600 represents an aggregate of an opportunity to improve the documentation of a patient case (e.g., an opportunity to correct under-documentation) and an opportunity to obtain clinical validation of documented condition(s) (e.g., an opportunity to correct over-documentation), as adjusted by various indicators and factors such that a patient case may, for example, move from one Medicare Severity-Diagnosis Related Group (MS-DRG) level to a higher reimbursing (more severe) MS-DRG level, reflecting the actual level of care provided to the patient.

Turning now to FIG. 7, process 700 may include determining a cumulative probability of an undocumented complication or comorbidity ("CC") (702) and determining a cumulative probability of an undocumented major CC (MCC) (704). CC and MCC represent different severity tiers of the MS-DRG classification system known to those skilled in the art. Different medical conditions found in the clinical data of a patient case may be classified at different severity tiers of the MS-DRG. For example, for heart failure, hyponatremia may be identified as a CC, while sepsis may be identified as a MCC. A payer's reimbursement structure may correspond to these severity tiers. For example, for heart failure, a payer may set a rate modifier of 1.49 at the base severity level, 1.78 at the CC severity level, and 2.3 at the MCC severity level.

In some embodiments, a machine learning model (e.g., a query prediction model) may be utilized to compute these cumulative probabilities based on at least the following exemplary input items:

Information about the patient (e.g., the patient's name, gender, length of stay, etc.).

A count of the number of progress notes by an attending physician in the particular patient case.

A count of the number of queries that have already been made in the particular patient case.

A count of undocumented medical conditions found in the particular patient case.

The most recently determined probability that a medical condition is present in the patient's case, as determined by the application of diagnostic model 211 during the most recent iteration of a case evaluation process (such as process 300 described above with reference to FIG. 3).

The most recently determined probability that a medical condition is not documented or not accurately documented, as determined by the application of documentation model 213 during the most recent iteration of a case evaluation process (such as process 300 described above with reference to FIG. 3).

The machine learning model is particularly configured to consider these input items, apply their associated weights, and determine a cumulative probability that the medical condition found in the clinical data of the patient case is actually an undocumented CC (702). For example, suppose the number of progress notes and the number of queries are weighted more than other input items, a medical condition that has already been queried and/or has too few progress notes in the patient case may have a low cumulative probability (e.g., less than 50%) that it indeed is an undocumented CC.

Likewise, the machine learning model can consider these input items, apply their associated weights, and determine a cumulative probability that the medical condition is an undocumented MCC (704). In some embodiments, the weights for the input items in determining the cumulative probability of an undocumented MCC may differ from those used in determining the cumulative probability of an undocumented CC.

The cumulative probabilities associated with potential diagnoses of undocumented CC and MCC are compared with the current DRG (which is indicative of the current diagnosis) for the patient case (706). In some embodiments, this comparison may further include determining differences between diagnostic states (e.g., the difference between the rate modifier of 1.49 at the base severity level and the rate modifier of 1.78 at the CC severity level, the difference between the rate modifier of 1.49 at the base severity level and the rate modifier of 2.3 at the MCC severity level, the difference between the rate modifier of 1.78 at the CC severity level and the rate modifier of 2.3 at the MCC severity level, etc.). Each rate modifier (also referred to as a weighting factor) may be stored in a table or other data structure, such as settings 130, corresponding to each medical condition. These predetermined weighting factors may reflect a host of clinical and economic concerns, such as hospital policies, gradients within payer reimbursement levels (e.g., cases where particular combinations of condition and diagnosis state are reimbursed significantly more or less), and/or, in some embodiments, the system's experience (e.g., medical conditions for which the system has a demonstrated aptitude for recognizing one or more types of CDI opportunities).

In some embodiments, each of these determined undocumented CC and undocumented MCC probabilities is weighed against the differences between diagnostic states and aggregated to return a result or score indicating a significance level of the under-documentation score (708). In some embodiments, an under-documentation score representing a possible CDI improvement may be dollar weighted and adjusted by the significance level thus generated. As an example, a 20% chance to find an additional $10,000 is a bigger opportunity ($2,000) than a 90% chance to find an additional $1000 ($900).

Similarly, process 800 may include determining a cumulative probability of a documented CC being valid or supported by the clinical data (802) and determining a cumulative probability of a documented MCC being valid or supported by the clinical data (804). The cumulative probabilities associated with documented CC and MCC are compared with the current DRG for the patient case (806). Each of the probabilities is weighed against the differences between diagnostic states and aggregated to return a result or score indicating a significance of the over-documentation score (808).

By way of clarifying example, suppose that for patient John Doe, performance of steps 302-312 shown in the example process 300 of FIG. 3 returns the following values, indicating that this patient may have hyponatremia and heart failure.

| Row No. | Condition | Diagnostic Probability (Probability Condition Exists) | Documentation Probability (Probability Condition Is Documented) |
|---|---|---|---|
| 1 | Hyponatremia (Base) | .94 | .89 |
| 2 | Hyponatremia (CC) | .76 | .24 |
| 3 | Hyponatremia (MCC) | .17 | .09 |
| 4 | Heart Failure (Base) | .83 | .91 |
| 5 | Heart Failure (CC) | .37 | .25 |
| 6 | Heart Failure (MCC) | .22 | .05 |

At step 702, the modeled CC probabilities for each of the patient's indicated conditions shown in rows 2 and 5 are fed to query prediction models to adjust, if necessary, the combined probabilities of 0.58 (=0.76*(1−0.24)) and 0.27 (=0.37*(1−0.75)) in view of the received information regarding recent reviews and other additional factors considered by query models to return a cumulative probability of an undocumented CC for each indicated condition. Suppose that the query prediction models indicate that no further modifications to the above probabilities of under-documentation are required, the process moves to step 704.

At step 704, the modeled MCC probabilities for each of the patient's indicated conditions shown in rows 3 and 6 are fed to query prediction models to adjust, if necessary, the combined probabilities of 0.15 (=0.17*(1−0.91)) and 0.21 (=0.22*(1−0.05)) in view of the received information regarding recent reviews and other additional factors considered by query models to return a cumulative probability of an undocumented MCC for each indicated condition. Suppose that the query prediction models indicate that no further modifications to the above probabilities of under-documentation are required, the process moves to step 706.

At step 706, the determined probabilities for each condition are compared against the current DRG for the patient. Suppose this patient's current DRG is a base level DRG, this may mean that the CDI score should be calculated for possibly shifting to a CC or MCC DRG. By Contrast, if this patient's current DRG is a CC level DRG, this may mean that the CDI score should be calculated for possibly shifting only to a MCC DRG, as the CC level diagnoses do not present any document improvement opportunities.

At step 708, a weighting factor for the current DRG family (which, in this example, refers to the heart failure DRG family) may be retrieved:

| Row No. | Condition | Weighting Factor |
|---|---|---|
| 1 | Heart Failure (Base) | 7.3 |
| 2 | Heart Failure (CC) | 9.7 |
| 3 | Heart Failure (MCC) | 25.6 |

For the current DRG, the "delta" between the current severity score and the next increment is multiplied by the previously determined probabilities that the conditions exist and is undocumented to determine an opportunity score for that particular documentation improvement opportunity.

For example, for Heart Failure (CC), there is a severity score difference of 2.4 between patient Doe's current diagnosis state (base, 7.3) and the potential more serious diagnosis (CC, 9.7). Multiplying this by the determined probability (0.15) that the CC exists and is undocumented, results in an under-documentation score of 0.36.

During the course of step 708, this determination is repeated for each identified CDI opportunity (which is presented via a medical condition at a particular severity level CC or MCC). Example results are shown below.

| CDI Opportunity | Under-Documentation Score |
|---|---|
| Hyponatremia (CC) | 0.05 |
| Hyponatremia (MCC) | 0.32 |
| Heart Failure (CC) | 0.36. |
| Heart Failure (MCC) | 3.74 |

The above values are then aggregated to return a numerical result (4.74), representing the overall significance of the opportunities for documentation improvement.

The overall significance of the opportunities for clinical validation (FIG. 8) can be computed in much the same way.

Specifically, at step 802, the modeled CC probabilities for each of the patient's indicated conditions shown in rows 2 and 5 are fed to query prediction models to adjust, if necessary, the combined probabilities of 0.06 (=(1−0.76)*0.24) and 0.16 (=(1−0.37)*0.25) in view of the received information regarding recent reviews and other additional factors considered by query models to return a cumulative probability of an over-documented CC for each indicated condition. Suppose that the query prediction models indicate that no further modifications to the above probabilities of over-documentation are required, the process moves to step 804.

At step 804, the modeled MCC probabilities for each of the patient's indicated conditions shown in rows 3 and 6 are fed to query prediction models to adjust, if necessary, the combined probabilities of 0.07 (=(1−0.17)*0.09) and 0.04 (=(1−0.22)*0.05) in view of the received information regarding recent reviews and other additional factors considered by query prediction models to return a cumulative probability of an over-documented MCC for each indicated condition. Suppose that the query prediction models indicate that no further modifications to the above probabilities of over-documentation are required, the process moves to step 806.

At step 806, the determined probabilities for each condition are compared against the current DRG for the patient. Suppose patient's two conditions (hyponatremia and heart failure) are currently indicated as being at the base level. This may mean no clinical validation opportunity exists.

At step 808, a weighting factor for each medical condition may be retrieved. These may be the same as or different from the weighting factors used in step 708 described above.

For the current DRG, the "delta" between the current significance score and the next increment is multiplied by the previously determined probabilities that the conditions exist and is undocumented to determine a clinical validation (over-documentation) score for that particular clinical validation opportunity.

For example, for heart failure (CC), there is a severity score difference of 2.4 between patient Doe's current condition and this improved condition. Multiplying this by the determined probability (0.15) that this condition does not exist, yet is somehow documented, results in a score of 0.36 for this clinical validation opportunity.

During the course of step 808, this determination is repeated for each identified CDI opportunity. Example results are shown below.

| CDI Opportunity | Over-Documentation Score |
|---|---|
| Hyponatremia (CC) | 0.005 |
| Hyponatremia (MCC) | 0.18 |
| Heart Failure (CC) | 0.16 |
| Heart Failure (MCC) | 0.53 |

The above values are then aggregated to return a numerical result (0.875), representing the overall significance of the opportunities for clinical validation.

The over-documentation score may serve as an obverse to the under-documentation score. Whereas an under-documentation score may suggest to a CDI specialist that they should "escalate" the patient's documentation (such as by changing the documentation to support a CC, or if a CC is indicated already, to support a MCC), an over-documentation score may "de-escalate," or clarify the patient's documentation (such as by changing the documentation that currently supports a MCC to either confirm the condition, or reduce documentation to indicate only a CC or lower diagnosis state).

Turning now to FIG. 9, which depicts a diagrammatic representation of an example set of special indicators 902 to be applied in a CDI scoring method according to some embodiments disclosed herein. As discussed herein, for policy, business, clinical or other reasons, there may be special indicators during a patient's visit, and the patient's case may be expected to be subject to greater scrutiny. Examples of such special indicators include, without limitation, visits to the intensive care unit, or emergency room, surgery and/or palliative care. In such cases, it may be desirable to ensure that a greater portion (or all) of such cases are prioritized for review by CDI specialists.

To this end, the determination of special indicators can provide a separate scoring mechanism that ensures that certain significant events can cause patient cases to appear in the priority list, independent of their calculated documentation improvement and/or clinical validation scores. Hospitals may use special indicators to encourage or force the review of patients who experience significant events, including, without limitation, surgeries, ICU transfers, palliative care orders, etc. The determined special indicators score may be compared with the adjusted determined CDI score and the greater of the two scores is returned as the final CDI score returned, for example, at step 322 in process 300 of FIG. 3.

In the example of FIG. 9, process 900 may include retrieving applicable special indicators 902 with their assigned values 904, aggregating assigned values 904, and generating a special indicators score.

By way of example, suppose that, as part of his hospital visit for treatment for hyponatremia and heart failure, patient John Doe also had surgery and stayed in the ICU. In such a case, CDI Scoring Engine 140 would return a special indicators score of 0.69 (0.23+0.46) to account for these events.

As discussed above, CDI scoring process 600 may further include performing one or more adjustments 1000, 1100, 1200 and/or 1300 to obtain a final CDI score. One such adjustment may include an adjustment for the patient's length of stay ("LOS"), or more particularly, the patient's expected temporal proximity to date of discharge.

Figure 10A:
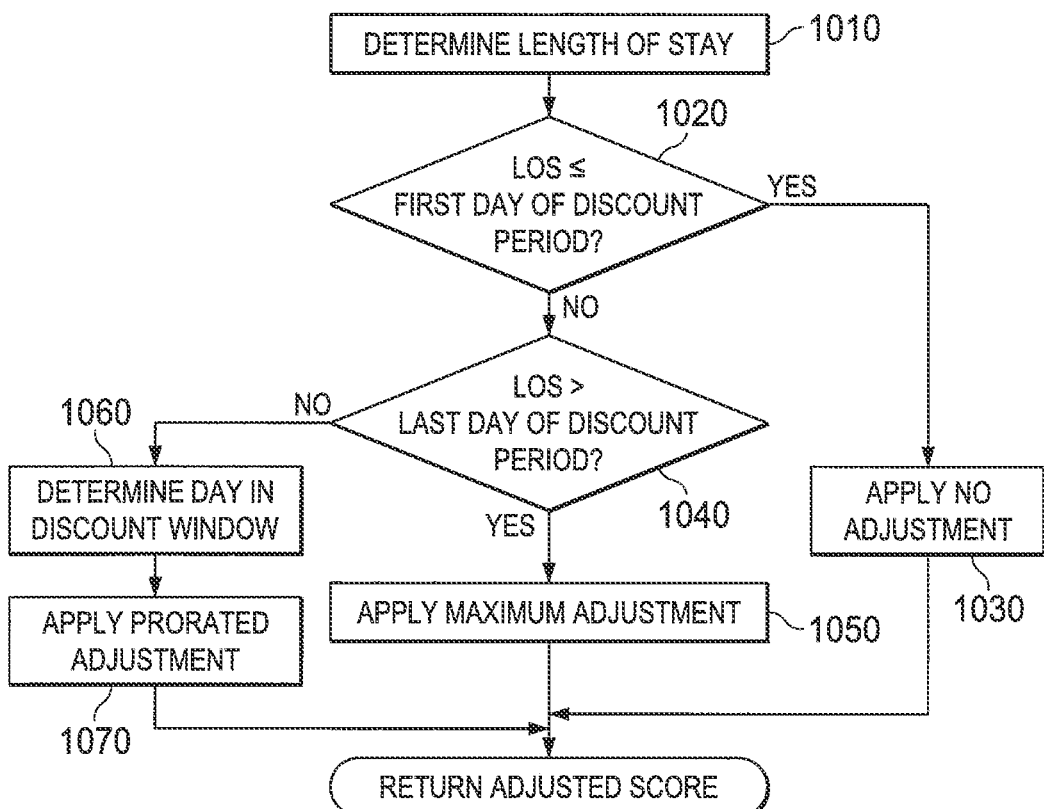
FIG. 10A is a flowchart illustrating one example of a process for determining a length of stay (LOS) adjustment to a system-generated CDI score according to some embodiments disclosed herein.

Turning now to FIG. 10A, which is a flowchart illustrating one example of a process for determining a length of stay (LOS) adjustment to a system-generated CDI score according to some embodiments disclosed herein. In some embodiments, the CDI scores may be generated in a way to incentivize reviewing patients prior to discharge.

According to some embodiments, adjusting a CDI score may be performed by first determining the length of the patient's stay (1010). This determination may be based on data received via HL7 gateway 129, or by data already resident in the patient case data stored in cases data store 150. Next, a determination is made as to whether the patient's length of stay is less than or equal to the first day of the discount period (1020). If yes, the process may proceed to step 1030, where no adjustment to the CDI score is performed, and an unadjusted CDI score is returned. If, however, the patient's LOS is not less than or equal to the first day of the discount period, a further determination is performed to see if the patient's LOS is greater than the last day of the discount period (1040). If so, the patient's case is outside of the adjustment window and process 1000 may proceed to step 1050, where a predetermined maximum discount is applied to the CDI score and a final CDI score thus adjusted is returned. If, at step 1040, the LOS is not greater than the last of the last day of the discount period, the patient's case is still in the adjustment window and, thus, process 1000 proceeds to step 1060, where the discount for the current day in the discount window is determined. Step 1060 may be performed through the application of a predefined discount function, such as one shown in FIG. 10B, discussed herein. Having determined the appropriate discount value, a prorated adjustment is applied to the CDI score at step 1070, and the adjusted CDI score is returned.

Figure 10B:
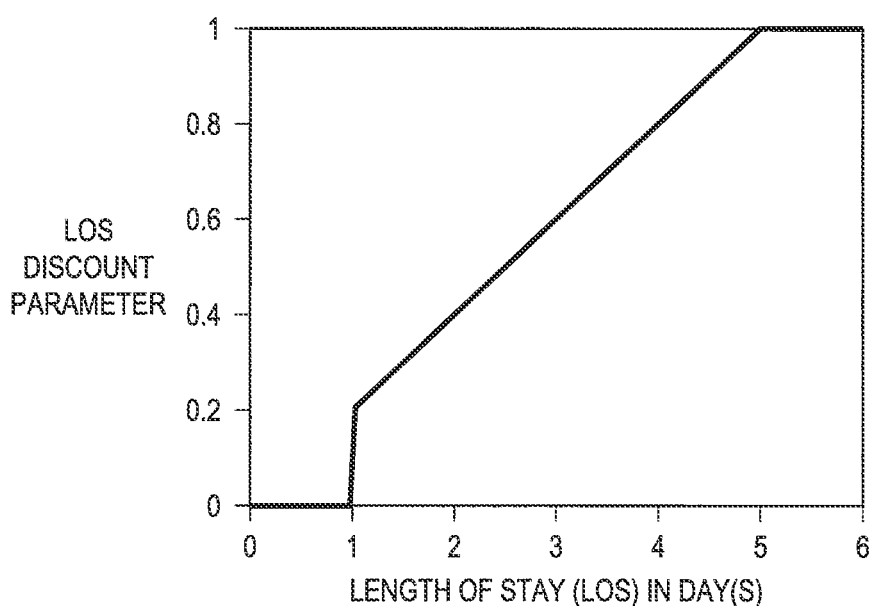
FIG. 10B is a plot diagram illustrating one example of an LOS discount function according to some embodiments disclosed herein.

Turning to FIG. 10B, which is a plot diagram illustrating one example of a LOS discount function according to some embodiments disclosed herein. In this example, the LOS discount function linearly discounts the opportunity so far computed the farther the case is from the expected discharge date based on the expected length of stay (LOS). A minimum LOS is defined before which the score will be discounted to 0. Once reaching the expected LOS, the CDI score is no longer discounted.

In some embodiments, three variables may control this LOS discount function:

1. The minimum length of stay—controls an initial window before which the opportunity is fully discounted (global parameter).
2. The y-intercept—controls the maximum discounting and the slope of the line, ranges from 1 (no discounting at all) to 0 (full discounting) (global parameter, default to 0).
3. Expected LOS—controls the point at which the score is no longer discounted.

In some embodiments, the CDI score may be multiplied by the LOS adjustment to arrive at an LOS adjusted opportunity. Unlike other adjustments, however, the LOS adjustment can have nothing to do with calculating either the potential magnitude of the CDI opportunity or the probability of realizing the CDI opportunity. Rather, it is made to adjust when CDI reviews are to take place. As such, the parameter values can be configurable based on a desired policy of a customer or client of the system.

Figure 11:
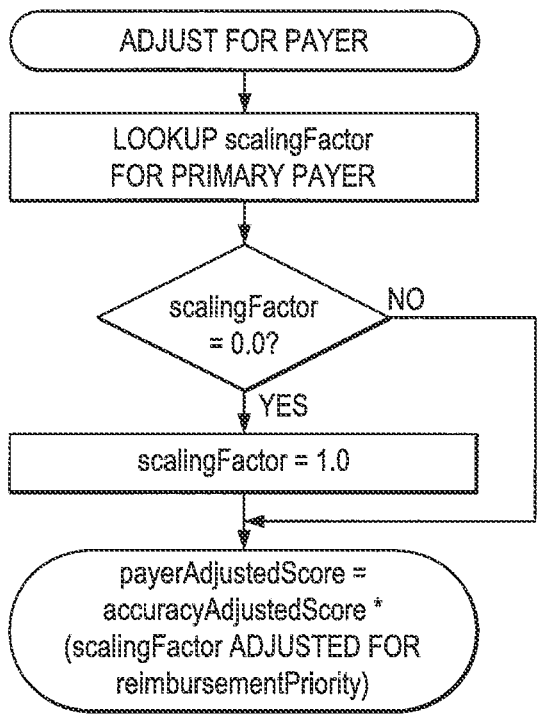
FIG. 11 is a flowchart illustrating one example of a process for determining a payer adjustment to a system-generated CDI score according to some embodiments disclosed herein.

According to some embodiments, the initial CDI score, which is shown as being determined at step 610 of FIG. 6, may be further adjusted to account for the impact of a payer adjustment. FIG. 11 shows one example of process 1100 for determining a payer adjustment to a system-generated CDI score, according to some embodiments disclosed herein.

In the example of FIG. 11, process 1100 may include looking up, from a table stored in a data store of system 100, such as global settings 133, a scaling factor associated with a primary payer for a patient's case. If the returned scaling factor has a value "0," the scaling factor is converted to a value of "1," resulting in no payer adjustment. If the returned scaling factor has a non-zero value, the returned scaling factor is multiplied by a CDI score, which, depending on embodiments, may be the initial CDI score returned at step 610 of FIG. 6, or to which other adjustment(s), such as for LOS, has/have already been applied.

A payer represents an entity that reimburses the hospital for a patient's care and is a multiplier based on reimbursement. For example, if Medicare reimburses $1000 and the payer reimburses $1100 for the same DRG, then that payer's adjustment factor is 1.1. If they reimburse $900 for the same DRG, then that payer's adjustment factor is 0.9.

For non-DRG payers, the default way to model non-DRG payers would be with an adjustment factor of 0. There may be some value in assigning a nominal value even to non-DRG payers, though non-DRG payers frequently still weigh the DRG in deciding whether claims are reasonable or not. Thus, there's the same incentive to make sure the highest value/most severe cases are documented correctly.

Example: Acme Hospital, with a payer adjustment factor for each payer as follows:

| Payer | Adjustment Factor |
| --- | --- |
| Medicare | 1 |
| Allied Health | .9 |

Example: Patient Jane Smith, adjusted to reflect a particular payer:

| | |
| --- | --- |
| Chief complaint: | cirrhosis w/ internal bleeding |
| LOS: | ? |
| Attending: | Dr. Smith |
| Payer: | Allied Health |
| Procedures: | 06180J9 Bypass Portal Vein to Right Renal Vein with Synthetic Substitute, Open Approach |
| Medications: | Lactulose |
| Conditions: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Target: | 4.405 |
| Probability Adjusted Opportunity: | 3.309 |
| Payer Adjusted Opportunity: | 3.309 * .9 = 2.978 |

In some embodiments, the CDI score determined at step 610 in the exemplary embodiment of FIG. 6 may be further adjusted to account for the patient's location within the hospital.

Certain locations in the hospital such as the ICU and telemetry may intrinsically adjust the case's priority in a query queue. If the system has the hospital's CMI by location, the system can calculate an adjustment factor for these locations; otherwise, the system may use assigned values for the severity adjustment (or not adjust by location at all). As with the payer factor, the severity factor is a multiplier applied to the adjusted opportunity.

Figure 12:
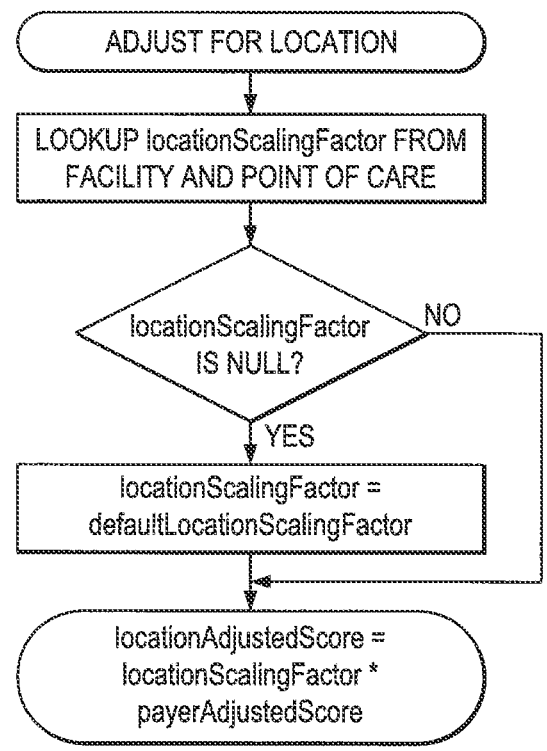
FIG. 12 is a flowchart illustrating one example of a process for determining a location adjustment to a system-generated CDI score according to some embodiments disclosed herein.

Turning now to FIG. 12, which is a flowchart illustrating one example of a process for determining a location adjustment to a system-generated CDI score according to some embodiments disclosed herein. In the example of FIG. 12, a method 1200 may be applied to determine and apply a location adjustment to a previously determined CDI score. According to method 1200, a location adjustment may be performed by looking up, from a table stored in a data store of real-time medical communication system 100, such as global settings 133, a scaling factor associated with one or a combination of hospital locations associated with the patient's case. If the returned scaling factor has a value "0," the scaling factor is converted to a value of "1," resulting in no location adjustment. If the returned scaling factor has a non-zero value, the returned scaling factor is multiplied by a CDI score, which, depending on embodiments, may be the CDI score returned at step 610 of FIG. 6, or to which other adjustment(s), such as for LOS or payer, has/have already been applied.

Example: Acme Hospital, which assigns a location-based severity adjustment factor for the ICU, as shown below:

| Location | Severity Adjustment Factor |
|---|---|
| ICU | 1.3 |

Example: Patient Jane Smith, adjusted to reflect the severity associated with the ICU location.

| | |
|---|---|
| Chief complaint: | cirrhosis w/ internal bleeding |
| LOS: | ? |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Conditions: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 2.978 * 1.3 = 3.871 |

Figure 13:
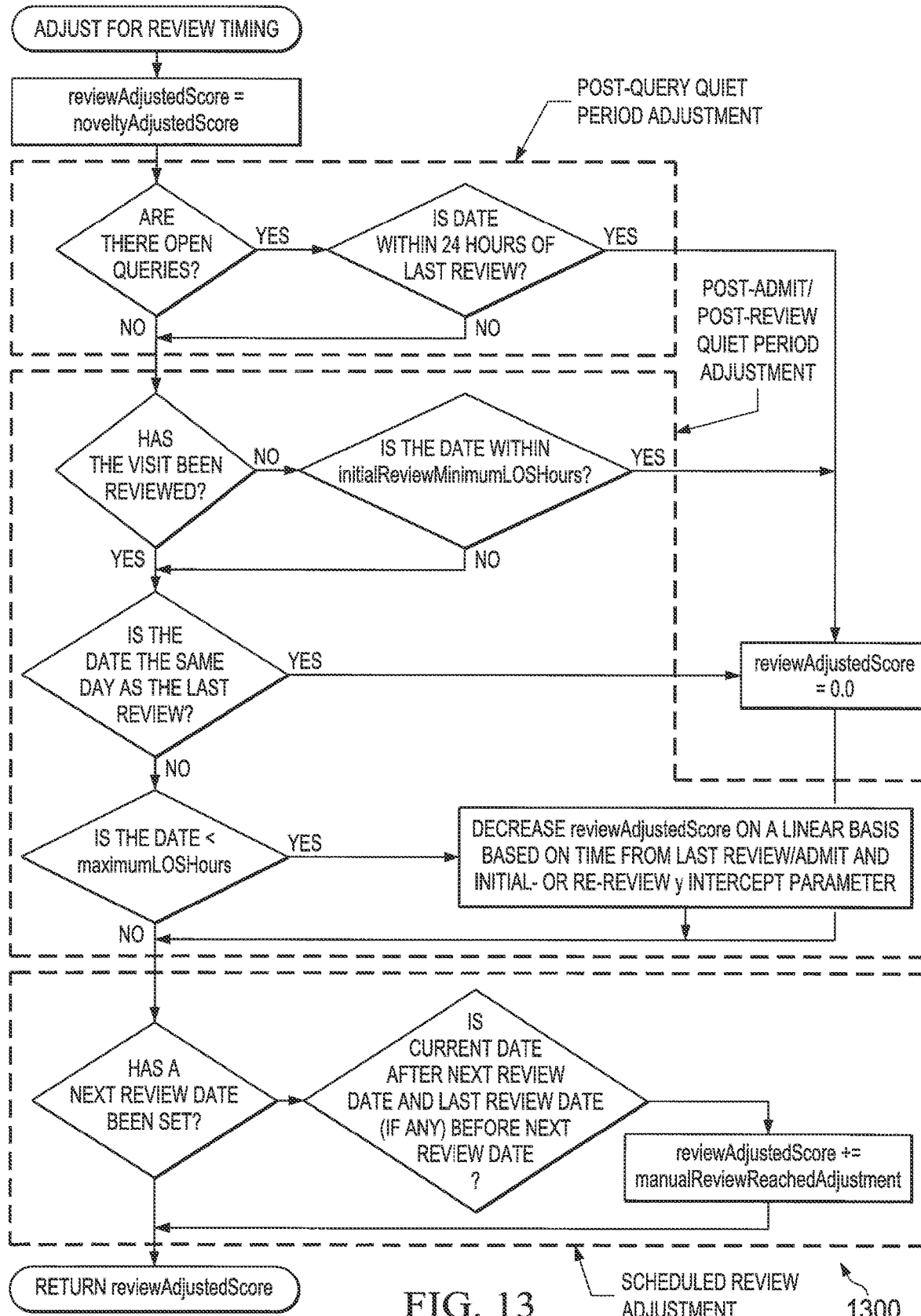
FIG. 13 is a flowchart illustrating one example of a process for determining a review timing adjustment to a system-generated CDI score according to some embodiments disclosed herein.

Turning now to FIG. 13, which is a flowchart illustrating one example of a process 1300 for determining a review timing adjustment to a system-generated CDI score according to some embodiments disclosed herein. According to some embodiments, the CDI score determined at step 610 may be further adjusted to incentivize a CDI review to be conducted at a predetermined optimum time. As noted herein, query opportunities may decrease significantly in the latter part of a patient's visit, particularly after the length of the patient's stay moves beyond one or more value. By the same token, the CDI may be highest during some portion of the initial part of a patient's stay. FIG. 13 provides an example of a method 1300 for adjusting the determined CDI score for a case to prioritize cases which may be in a temporal "sweet spot" for CDI review and querying.

In the non-limiting example of FIG. 13, adjustment for review timing 1300 comprises three underlying determinations, each demarcated in FIG. by dotted boxes. These determinations comprise: 1.) determining a CDI adjustment based on open/recent queries; 2.) adjusting based on past review; and 3.) an adjustment for scheduled review dates.

With reference to the example shown in FIG. 13, the initial determination of a CDI adjustment based on open/recent queries determines a.) whether there are any open queries in the case, and b.) if less than 24 hours have elapsed since the last query/review. If the answer to either of these questions is "Yes"—a CDI adjustment multiplier of "0" is applied to the case. Multiplying the CDI score by zero completely de-prioritizes the case, and puts the case in a "quiet period" during which there is no need to determine the existence and magnitude of query opportunities.

If the answer to both queries regarding open queries and whether the date is within 24 hours of the last review is "No," process 1300 moves onto the second line of inquiry—adjusting in cases where there has been a past review.

This second inquiry proceeds through the following steps: initially determining if the visit has been reviewed and confirming that the duration of the patient's stay has hit a minimum threshold for review. If these conditions are satisfied, a determination as to whether the current data is the same as the date of the last review. If the visit has been recently reviewed or the length of stay falls short of the length of stay, the case is put into a post-review/post-admit quiet period, and a query adjustment multiplier of "0" is applied to the case, thereby temporarily setting the CDI score for the case to zero. If the date falls between predetermined minimums and maximums for length of stay and/or interval since the last review, a discounting function is applied to the CDI score. In the example of FIG. 13, the discounting function is a linear function.

Process 1300 as it applies to the past review/length of stay adjustment may be further explained through the following example:

In some cases, a customer or client of the system may want to incentivize a process where an initial CDI review takes place (for example, at the 24 to 48 hour mark) followed by a re-review prior to discharge. To accomplish this goal, the system may use two separate versions of this function with different values. The first version applies to cases which have never been reviewed and the second version applies to cases that have previously been reviewed.

For example, for cases that have never been reviewed, the system may use the values min LOS: 1 (do not review before 24 hours), y-intercept: 1 (no discounting at all beyond the first 24 hours), expected LOS: 2 (if discounting reach the maximum by the end of 48 hours) and for cases that have been reviewed, the system may use the values min LOS: 1 (do not review before 24 hours), y-intercept: 0 (full discounting), expected LOS: 5 (reaching the maximum by 5 days into the stay).

Example: Acme Hospital

| | |
|---|---|
| Minimum LOS before review: | 1 |
| y-intercept: | 0 |
| Mean expected LOS: | 5 |
| MS-DRG | GMLOS |
| pancreas, liver and shunt procedures w/ MCC | 11.337 |

Example: Patient Jane Smith

| | |
|---|---|
| Chief complaint: | cirrhosis w/ internal bleeding |
| LOS: | 6 |
| Attending: | Dr. Smith |
| Location: | ICU |
| Payer: | Allied Health |
| Procedures: | 06180J9 Bypass Portal Vein to Right Renal Vein with Synthetic Substitute, Open Approach |
| Medications: | Lactulose |
| Conditions: | Liver procedure (base DRG: pancreas, liver and shunt procedures, relative weight 1.828) Malnutrition (MCC, pancreas, liver and shunt procedures w/ MCC has relative weight 5.575) |
| Baseline: | 1.096 |
| Target: | 5.94 |
| Unadjusted Opportunity: | 4.844 |
| Probability Adjusted Opportunity: | 3.309 |
| Payer Adjusted Opportunity: | 2.978 |
| Location Adjusted Opportunity: | 3.871 |
| Location Adjusted Opportunity (last review): | .805 |
| Novelty Adjusted Opportunity: | 3.227 |
| Adjusted Opportunity: | 3.227 * ((1.0 − 0) * 6 / 11) + 0 = 1.760 |

Finally, in process 1300, where a review date has been set, and the case has not yet been reviewed, the CDI score may be adjusted upward through the use of a predetermined and/or manually set adjustment factor, thereby ensuring that the case is queried.

Furthermore, in some embodiments, the CDI scoring method described above (which examines clinical evidence received by the system to determine how to prioritize cases for CDI review) may be adapted to factor in the amount of effort needed by a CDI specialist to review a patient case due to the size/amount of documentation involved. A case size adjustment may be determined based at least in part on statistics collected about how much documentation there is for a patient case. For example, a patient who has been in a hospital for 50 days and has 300 pages of documentation requires a much bigger effort for a CDI specialist to review than a case that just arrived yesterday.

The CDI score thus generated for a patient's case may reflect the total likelihood that a documentation issue (e.g., under- or over-documentation) exists and that querying the underlying documentation issue will have a meaningful impact on the documentation of the case. Examples of document improvements having a meaningful impact may include documentation changes that result in changes to the net amount billed to a payer that exceeds predefined thresholds. A high under-documentation score may indicate an opportunity for an "impact," "quality," or "severity" query to determine whether the documentation may be augmented or clarified to appropriately account for clinical conditions that exist. A high over-documentation score may indicate an opportunity for a "clinical validation" query, in which the documentation needs to be corrected to only account for the conditions which the patient actually has.

A significant document improvement opportunity may arise in situations where the patient's condition supports a diagnosis state having a higher complication or comorbidity level than is reflected in the current documentation. For example, for conditions having a MS-DRG diagnosis, the level of Medicare reimbursement may remain unchanged through an initial range of diagnosis states, but may jump suddenly when the patient's condition carries an indication of a CC and/or a MCC. As a non-limiting example, within the DRG for renal failure, there may be five diagnostic states. Of these, states 1-3 represent distinctions of principally clinical interest, and which are equally reimbursed by Medicare. State 4 may reflect a CC, such as renal failure for which a patient needs to take medication, and state 5 may reflect a MCC, such as end-stage renal failure requiring dialysis. A case in which a patient has been prescribed medication, but whose documentation currently only supports "State 3" renal failure would represent a document improvement opportunity, as the patient's newly prescribed medication makes "State 4" the correct diagnostic state. Because, in this example, "Renal Failure—State 4" is reimbursed differently than "Renal Failure—State 3," there is a document improvement opportunity associated with the under-documentation in this case.

A significant clinical validation opportunity may arise, when the documentation in the case indicates one or more conditions having a severity level beyond that which is shown in the clinical documentation. Over-documentation may occur in cases in which the documentation improperly reports multiple conditions based on a given set of indicators, or the documentation indicates that a single condition is more severe (i.e., reports a "CC" or "MCC") for a milder case.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

Embodiments discussed herein can be implemented in a computer communicatively coupled to a network (for example, the Internet), another computer, or in a standalone computer. As is known to those skilled in the art, a suitable computer can include a central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylus, touch pad, etc.), or the like.

ROM, RAM, and HD are computer memories for storing computer-executable instructions executable by the CPU or capable of being compiled or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. The processes described herein may be implemented in suitable computer-executable instructions that may reside on a computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including C, C++, Java, JavaScript, HTML, or any other programming or scripting code, etc. Other software/hardware/network architectures may be used. For example, the functions of the disclosed embodiments may be implemented on one computer or shared/distributed among two or more computers in or across a network. Communications between computers implementing embodiments can be accomplished using any electronic, optical, radio frequency signals, or other suitable methods and tools of communication in compliance with known network protocols.

Different programming techniques can be employed such as procedural or object oriented. Any particular routine can execute on a single computer processing device or multiple computer processing devices, a single computer processor or multiple computer processors. Data may be stored in a single storage medium or distributed through multiple storage mediums, and may reside in a single database or multiple databases (or other data storage techniques). Although the steps, operations, or computations may be presented in a specific order, this order may be changed in different embodiments. In some embodiments, to the extent multiple steps are shown as sequential in this specification, some combination of such steps in alternative embodiments may be performed at the same time. The sequence of operations described herein can be interrupted, suspended, or otherwise controlled by another process, such as an operating system, kernel, etc. The routines can operate in an operating system environment or as stand-alone routines. Functions, routines, methods, steps and operations described herein can be performed in hardware, software, firmware or any combination thereof.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

It is also within the spirit and scope of the invention to implement in software programming or code an of the steps, operations, methods, routines or portions thereof described herein, where such software programming or code can be stored in a computer-readable medium and can be operated on by a processor to permit a computer to perform any of the steps, operations, methods, routines or portions thereof described herein. The invention may be implemented by using software programming or code in one or more digital computers, by using application specific integrated circuits, programmable logic devices, field programmable gate arrays, optical, chemical, biological, quantum or nanoengineered systems, components and mechanisms may be used. In general, the functions of the invention can be achieved by any means as is known in the art. For example, distributed, or networked systems, components and circuits can be used. In another example, communication or transfer (or otherwise moving from one place to another) of data may be wired, wireless, or by any other means.

A "computer-readable medium" may be any medium that can contain, store, communicate, propagate, or transport the program for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory. Such computer-readable medium shall be machine readable and include software programming or code that can be human readable (e.g., source code) or machine readable (e.g., object code). Examples of non-transitory computer-readable media can include random access memories, read-only memories, hard drives, data cartridges, magnetic tapes, floppy diskettes, flash memory drives, optical data storage devices, compact-disc read-only memories, and other appropriate computer memories and data storage devices. In an illustrative embodiment, some or all of the software components may reside on a single server computer or on any combination of separate server computers. As one skilled in the art can appreciate, a computer program product implementing an embodiment disclosed herein may comprise one or more non-transitory computer readable media storing computer instructions translatable by one or more processors in a computing environment.

A "processor" includes any hardware system, mechanism or component that processes data, signals or other information. A processor can include a system with a central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc.

Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited to only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the claims that follow, the meaning of "in" includes "in" and "on" unless the context clearly dictates otherwise. The scope of this disclosure should be determined by the following claims and their legal equivalents.

What is claimed is:

1. A method, comprising:
   receiving, by a clinical documentation improvement (CDI) system, real-time medical data from a data source, the real-time medical data comprising clinical data for a patient and documentation for a visit of the patient;
   determining, by the CDI system based on the real-time medical data, a medical condition for the patient;
   determining, by the CDI system utilizing the real-time medical data, a difference between portions of the real-time medical data and stored data items the CDI system has for the visit of the patient;
   determining, by the CDI system based on the difference between the portions of the real-time medical data and the stored data items the CDI system has for the visit of the patient, a machine learning diagnosis model and a machine learning documentation model for analyzing the medical condition for the patient, the machine learning diagnosis model and a machine learning documentation model selected from a set of condition models for the medical condition;
   generating, by the CDI system, an under-documentation score for the medical condition by applying the machine learning diagnosis model to the portions of the real-time medical data, the under-documentation score representing a probability that the medical condition is clinically valid but is not sufficiently documented;
   generating, by the CDI system, an over-documentation score for the medical condition by applying the machine learning documentation model to the stored data items the CDI system has for the visit of the patient, the over-documentation score representing a probability that the medical condition is documented but is not supported by the clinical data for the patient; and
   generating, by the CDI system based at least in part on the under-documentation score and the over-documentation score, a CDI score for the visit of the patient.

2. The method of claim 1, further comprising:
   determining special indicators applicable to the visit of the patient, wherein the special indicators represent significant events during the visit of the patient;
   aggregating values of the special indicators; and
   generating a special indicators score based on the values of the special indicators thus aggregated, wherein generating the CDI score for the visit of the patient further includes combining the under-documentation score for the medical condition, the over-documentation score for the medical condition, and the special indicators score.

3. The method of claim 2, wherein the special indicators score is independent of the under-documentation score for the medical condition, the over-documentation score for the medical condition, or a combination thereof.

4. The method of claim 1, further comprising:
   evaluating the under-documentation score for the medical condition in conjunction with a queryability factor that represents a consideration applicable to the visit of the patient; and
   determining an overall under-documentation score based at least in part on the evaluating.

5. The method of claim 1, further comprising:
   aggregating over-documentation scores across medical conditions in the data set for the visit of the patient; and
   generating an overall over-documentation score based on the over-documentation scores thus aggregated.

6. The method of claim 1, further comprising:
   determining a cumulative probability that the medical condition determined from the real-time medical data is an undocumented complication or comorbidity, the determining the cumulative probability based at least in part on information about the patient, a number of progress notes by an attending physician for the patient, a number of queries made to the stored data items the CDI system has for the visit of the patient, or a count of undocumented medical conditions found in the stored data items the CDI system has for the visit of the patient.

7. The method of claim 1, further comprising:
   adjusting the CDI score for the visit of the patient based at least in part on a location of the patient.

8. A clinical documentation improvement (CDI) system, comprising:
   a processor;
   a non-transitory computer readable medium; and
   stored instructions translatable by the processor to perform:
      receiving real-time medical data from a data source, the real-time medical data comprising clinical data for a patient and documentation for a visit of the patient;
      determining, based on the real-time medical data, a medical condition for the patient;
      determining, utilizing the real-time medical data, a difference between portions of the real-time medical data and stored data items the CDI system has for the visit of the patient;
      determining, based on the difference between the portions of the real-time medical data and the stored data items the CDI system has for the visit of the patient, a machine learning diagnosis model and a machine learning documentation model for analyzing the medical condition for the patient, the machine learning diagnosis model and a machine learning documentation model selected from a set of condition models for the medical condition;

generating, an under-documentation score for the medical condition by applying the machine learning diagnosis model to the portions of the real-time medical data, the under-documentation score representing a probability that the medical condition is clinically valid but is not sufficiently documented;

generating, an over-documentation score for the medical condition by applying the machine learning documentation model to the stored data items the CDI system has for the visit of the patient, the over-documentation score representing a probability that the medical condition is documented but is not supported by the clinical data for the patient; and generating, based at least in part on the under-documentation score and the over-documentation score, a CDI score for the visit of the patient.

9. The CDI system of claim 8, wherein the stored instructions are further translatable by the processor to perform:

determining special indicators applicable to the visit of the patient, wherein the special indicators represent significant events during the visit of the patient;

aggregating values of the special indicators; and generating a special indicators score based on the values of the special indicators thus aggregated, wherein generating the CDI score for the visit of the patient further includes combining the under-documentation score for the medical condition, the over-documentation score for the medical condition, and the special indicators score.

10. The CDI system of claim 9, wherein the special indicators score is independent of the under-documentation score for the medical condition, the over-documentation score for the medical condition, or a combination thereof.

11. The CDI system of claim 8, wherein the stored instructions are further translatable by the processor to perform:

evaluating the under-documentation score for the medical condition in conjunction with a queryability factor that represents a consideration applicable to the visit of the patient; and determining an overall under-documentation score based at least in part on the evaluating.

12. The CDI system of claim 8, wherein the stored instructions are further translatable by the processor to perform:

aggregating over-documentation scores across medical conditions in the data set for the visit of the patient; and generating an overall over-documentation score based on the over-documentation scores thus aggregated.

13. The CDI system of claim 8, wherein the stored instructions are further translatable by the processor to perform:

determining a cumulative probability that the medical condition determined from the real-time medical data is an undocumented complication or comorbidity, the determining the cumulative probability based at least in part on information about the patient, a number of progress notes by an attending physician for the patient, a number of queries made to the stored data items the CDI system has for the visit of the patient, or a count of undocumented medical conditions found in the stored data items the CDI system has for the visit of the patient.

14. The CDI system of claim 8, wherein the stored instructions are further translatable by the processor to perform:

adjusting the CDI score for the visit of the patient based at least in part on a location of the patient.

15. A computer program product comprising a non-transitory computer-readable medium storing instructions translatable by a processor of a clinical documentation improvement (CDI) system to perform:

receiving real-time medical data from a data source, the real-time medical data comprising clinical data for a patient and documentation for a visit of the patient;

determining, based on the real-time medical data, a medical condition for the patient;

determining, utilizing the real-time medical data, a difference between portions of the real-time medical data and stored data items the CDI system has for the visit of the patient;

determining, based on the difference between the portions of the real-time medical data and the stored data items the CDI system has for the visit of the patient, a machine learning diagnosis model and a machine learning documentation model for analyzing the medical condition for the patient, the machine learning diagnosis model and a machine learning documentation model selected from a set of condition models for the medical condition;

generating, an under-documentation score for the medical condition by applying the machine learning diagnosis model to the portions of the real-time medical data, the under-documentation score representing a probability that the medical condition is clinically valid but is not sufficiently documented;

generating, an over-documentation score for the medical condition by applying the machine learning documentation model to the stored data items the CDI system has for the visit of the patient, the over-documentation score representing a probability that the medical condition is documented but is not supported by the clinical data for the patient; and generating, based at least in part on the under-documentation score and the over-documentation score, a CDI score for the visit of the patient.

16. The computer program product of claim 15, wherein the instructions are further translatable by the processor to perform:

determining special indicators applicable to the visit of the patient, wherein the special indicators represent significant events during the visit of the patient;

aggregating values of the special indicators; and generating a special indicators score based on the values of the special indicators thus aggregated, wherein generating the CDI score for the visit of the patient further includes combining the under-documentation score for the medical condition, the over-documentation score for the medical condition, and the special indicators score.

17. The computer program product of claim 15, wherein the special indicators score is independent of the under-documentation score for the medical condition, the over-documentation score for the medical condition, or a combination thereof.

18. The computer program product of claim 15, wherein the instructions are further translatable by the processor to perform:
- evaluating the under-documentation score for the medical condition in conjunction with a queryability factor that represents a consideration applicable to the visit of the patient; and
- determining an overall under-documentation score based at least in part on the evaluating.

19. The computer program product of claim 15, wherein the instructions are further translatable by the processor to perform:
- aggregating over-documentation scores across medical conditions in the data set for the visit of the patient; and
- generating an overall over-documentation score based on the over-documentation scores thus aggregated.

20. The computer program product of claim 15, wherein the instructions are further translatable by the processor to perform:
- determining a cumulative probability that the medical condition determined from the real-time medical data is an undocumented complication or comorbidity, the determining the cumulative probability based at least in part on information about the patient, a number of progress notes by an attending physician for the patient, a number of queries made to the stored data items the CDI system has for the visit of the patient, or a count of undocumented medical conditions found in the stored data items the CDI system has for the visit of the patient.

* * * * *